United States Patent
Soskey et al.

(10) Patent No.: US 9,782,776 B2
(45) Date of Patent: Oct. 10, 2017

(54) COLLECTION CONTAINER ASSEMBLY WITH NANOCOMPOSITE BARRIER COATING

(75) Inventors: Paul R. Soskey, Branchburg, NJ (US); Jerome F. Parmer, Jr., Chester, NJ (US); Harris A. Goldberg, Edison, NJ (US); Douglas P. Karim, Irvine, CA (US); Laxmi Samantara, Edison, NJ (US); Carrie A. Feeney, Bridgewater, NJ (US); Michele Farrell, Bethlehem, PA (US)

(73) Assignee: INMAT, INC., Hillsborough, NJ (US)

(*) Notice: Subject to any disclaimer, the term of this patent is extended or adjusted under 35 U.S.C. 154(b) by 2163 days.

(21) Appl. No.: 12/383,058

(22) Filed: Mar. 19, 2009

(65) Prior Publication Data

US 2009/0285722 A1    Nov. 19, 2009

Related U.S. Application Data

(60) Provisional application No. 61/070,128, filed on Mar. 20, 2008.

(51) Int. Cl.
*B01L 3/14*     (2006.01)
*B01L 3/00*     (2006.01)
(Continued)

(52) U.S. Cl.
CPC ...... *B01L 3/50825* (2013.01); *A61B 5/15003* (2013.01); *A61B 5/154* (2013.01);
(Continued)

(58) Field of Classification Search
CPC .................................. A61B 5/14; B01L 3/14
See application file for complete search history.

(56) References Cited

U.S. PATENT DOCUMENTS

| 4,830,217 A | 5/1989 | Dufresne et al. ............ 220/420 |
| 5,725,909 A | 3/1998 | Shaw et al. ................ 427/412.1 |

(Continued)

FOREIGN PATENT DOCUMENTS

| EP | 0 164 583 A2 | 12/1985 | ............ B32B 27/00 |
| EP | 0 787 824 A2 | 8/1997 | ............ C23C 16/40 |

(Continued)

OTHER PUBLICATIONS

International Preliminary Report on Patentability.
(Continued)

*Primary Examiner* — Randy Boyer
(74) *Attorney, Agent, or Firm* — Michael W. Ferrell

(57) ABSTRACT

An evacuated container assembly suitable for use in connection with blood collection including: (a) a container member formed of a first polymeric material and having a sidewall and one or more openings; (b) a nanocomposite barrier coating disposed on the container member having a thickness of up to about 30 microns and being derived from an aqueous dispersion including (i) a dispersed barrier matrix polymer; and (ii) a substantially exfoliated silicate filler having an aspect ratio of more than 50; and (c) one or more sealing members disposed in the opening(s) operative to hermetically seal the cavity; wherein the cavity is evacuated and maintains a pressure below atmospheric pressure and exhibits a draw volume loss lower than that of a like assembly without a nanocomposite barrier film by a factor of at least 1.5.

58 Claims, 27 Drawing Sheets

(51) Int. Cl.
*A61B 5/15* (2006.01)
*A61B 5/154* (2006.01)

(52) U.S. Cl.
CPC .. *A61B 5/150274* (2013.01); *A61B 5/150351* (2013.01); *A61B 5/150755* (2013.01); *B01L 2200/12* (2013.01); *B01L 2200/141* (2013.01); *B01L 2200/16* (2013.01); *B01L 2300/044* (2013.01); *B01L 2300/12* (2013.01); *B01L 2300/16* (2013.01); *B01L 2300/161* (2013.01); *B01L 2300/168* (2013.01)

(56) References Cited

U.S. PATENT DOCUMENTS

| | | | | |
|---|---|---|---|---|
| 5,849,830 | A | 12/1998 | Tsipursky et al. | 524/450 |
| 5,871,700 | A | 2/1999 | Konrad | 422/102 |
| 5,925,428 | A | 7/1999 | Hubbard et al. | 428/34.5 |
| 5,955,161 | A | 9/1999 | Tropsha | |
| 6,077,235 | A * | 6/2000 | Serpentino et al. | 600/573 |
| 6,354,452 | B1 | 3/2002 | DeSalvo et al. | 220/23.87 |
| 6,651,835 | B2 | 11/2003 | Iskra | 220/23.87 |
| 6,749,078 | B2 | 6/2004 | Iskra | 220/23.87 |
| 6,881,526 | B2 | 4/2005 | Bobeck et al. | 430/30 |
| 7,303,797 | B1 | 12/2007 | Barsotti et al. | |
| 7,323,889 | B2 | 1/2008 | Pfaff et al. | 324/752 |
| 2005/0037165 | A1* | 2/2005 | Ahern et al. | 428/35.7 |
| 2005/0037231 | A1 | 2/2005 | Jones et al. | |
| 2005/0214659 | A1 | 9/2005 | Andrews et al. | |
| 2006/0094810 | A1 | 5/2006 | Kim et al. | |
| 2006/0121228 | A1 | 6/2006 | Kim et al. | 428/36.9 |
| 2008/0131707 | A1 | 6/2008 | Feeney et al. | |
| 2010/0181315 | A1 | 7/2010 | Imoda et al. | |

FOREIGN PATENT DOCUMENTS

| | | |
|---|---|---|
| JP | H09253077 A | 9/1997 |
| JP | 2000336303 A | 12/2000 |
| JP | 2002537148 A | 11/2002 |
| JP | 2003508274 A | 3/2003 |
| JP | 2004532756 A | 10/2004 |
| JP | 2005324461 A | 11/2005 |
| JP | 2006503963 A | 2/2006 |
| JP | 2007039060 A | 2/2007 |
| JP | 2007504297 A | 3/2007 |
| WO | WO 99/32403 | 7/1999 ............ C01B 33/44 |
| WO | 0009596 A1 | 2/2000 |
| WO | 0049072 A1 | 8/2000 |
| WO | WO 01/17774 | 3/2001 ............ B32B 31/12 |
| WO | 0187566 A1 | 11/2001 |
| WO | WO 2004/037888 | 5/2004 ............ C08G 63/00 |
| WO | 2005044938 A2 | 5/2005 |
| WO | 2005108070 A2 | 11/2005 |
| WO | 2006115729 A1 | 11/2006 |
| WO | WO 2007/062391 | 5/2007 ............ C08K 3/22 |
| WO | WO 2007/062391 A2 | 5/2007 ............ C08K 3/22 |
| WO | 2007088815 A1 | 8/2007 |
| WO | 2007142720 A1 | 12/2007 |
| WO | WO 2009/114072 | 9/2009 ............ C08K 3/34 |

OTHER PUBLICATIONS

Ward, W J et al: "Gas Barrier Improvement Using Vermiculite and Mica in Polymer Films", Journal of Membrane Science, Jan. 1, 1991, pp. 173-180, vol. 55, No. 1/02, Elsevier BV, NL.

First Communication in European Counterpart EP09722389, dated Feb. 10, 2017.

English translation of Office Action from counterpart Japanese patent application, dated Jan. 27, 2017.

Robert D. Leaversuch, Barrier PET Bottles: "No Breakthrough in Beer, But Juice & Soda Surge Ahead", Plastics Technology, Mar. 2003, pp. 1-5.

* cited by examiner

DRAW VOLUME LOSS OF BARRIER COATED PP TUBES WITH PET CONTROLS AT 40°C

QUALITATIVE TAPE TEST RESULT OF COATING ON ENERCON TREATED PP TUBES

NIR DYE SDA 8700 IN WATER (ABSORBANCE-LINEAR BASELINE)

(ABSORBANCE-POLYNOMIAL BASELINE)

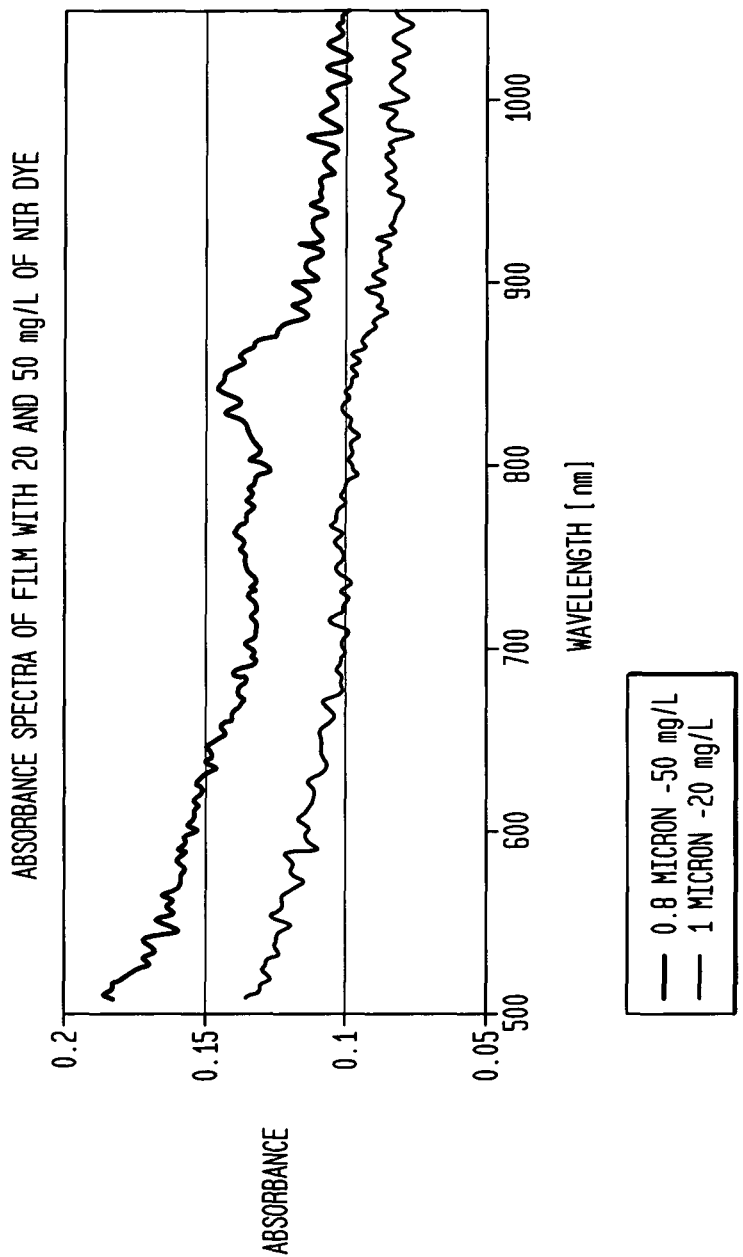

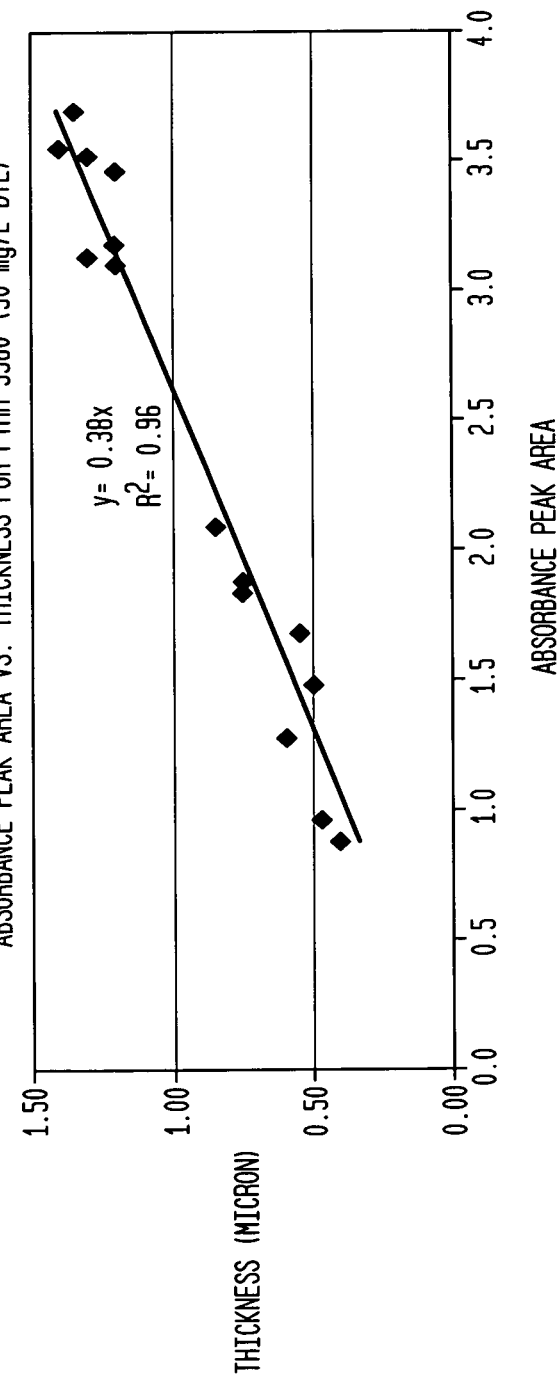

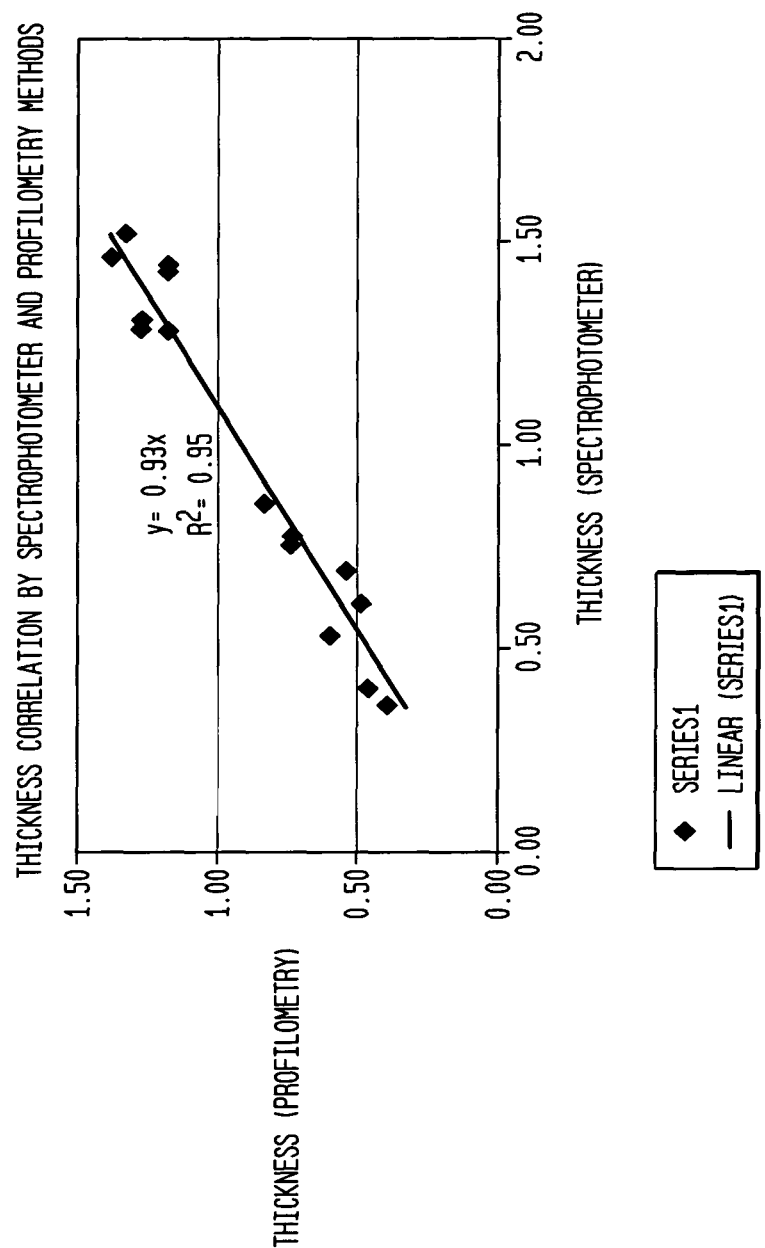

US 9,782,776 B2

COLLECTION CONTAINER ASSEMBLY WITH NANOCOMPOSITE BARRIER COATING

CLAIM FOR PRIORITY

This non-provisional application claims the benefit of the filing date of U.S. Provisional Patent Application Ser. No. 61/070,128, of the same title, filed Mar. 20, 2008. The priority of U.S. Provisional Patent Application Ser. No. 61/070,128 is hereby claimed and the disclosure thereof is incorporated into this application by reference.

FIELD OF INVENTION

This application relates to a plastic collection container assembly including a nanocomposite barrier coating to reduce permeability of gasses and increase shelf life.

BACKGROUND OF THE INVENTION

Plastic tubes have an inherent permeability to transport of gasses and/or water vapor due to the physical properties of the plastic materials used in manufacturing such tubes. Therefore, it is especially difficult to maintain the shelf-life of evacuated plastic tubes that contain a liquid additive of the class used in connection with blood collection. It is also appreciated that deterioration of the volume and concentration of the liquid additive may interfere with the intended use of the tube. Sometimes hybrid assemblies are used for blood collection, including both a polyethylene terephthalate tube for oxygen and other gas barrier and a polypropylene tube for water barrier. Such assemblies are relatively expensive for disposable articles and are relatively difficult to recycle. While barrier properties can be improved somewhat by using more material, this too adds cost which is particularly undesirable in disposable products.

In addition, plastic tubes that are used for blood collection require certain performance standards to be acceptable for use in medical applications. Such performance standards include the ability to maintain greater than about 90% original draw volume over a one-year period, to be radiation sterilizable and to be non-interfering in tests and analysis.

SUMMARY OF THE INVENTION

An evacuated container assembly suitable for use in connection with blood collection includes: (a) a container member formed of a first polymeric material and having a sidewall defining a collection interior with an inner surface; (b) a nanocomposite barrier coating disposed on the container member having a thickness of up to about 30 microns and being derived from an aqueous dispersion including (i) a dispersed barrier matrix polymer; and (ii) a substantially exfoliated silicate filler having an aspect ratio of more than 50; and (c) one or more sealing member(s) disposed in the opening operative to hermetically seal the interior. The cavity is evacuated and maintains a pressure below atmospheric pressure and exhibits a draw volume loss lower than that of a like assembly without a nanocomposite barrier film by a factor of at least 1.5.

Also provided are barrier-coated tubes suitable for use in container assemblies and methods of producing them.

One method of preparing the nanocomposite coatings involves evaporating water from an aqueous dispersion to increase the solids content of the dispersion prior to dip-coating a tube.

In another aspect, there are provided sample tubes having a nanocomposite barrier coating with an invisible marker dye operable to indicate thickness of the coating. In such cases both the tube and coating may be transparent with respect to visual light and absorbing with respect to near infra-red light.

Still further features and advantages of the invention are apparent from the following description.

BRIEF DESCRIPTION OF THE DRAWINGS

The invention is described in detail below with reference to the drawings wherein:

FIG. 22 is a plot of absorbance vs. wavelength in nanometers for a 1 micron thick and a 0.8 thick micron coating;

FIG. 23 is a plot of thickness vs. absorbent peak area; and

FIG. 24 is a plot of thickness as measured by profilometry vs. thickness determined by a spectral photometer in accordance with the invention.

DETAILED DESCRIPTION OF THE INVENTION

Figure 1:
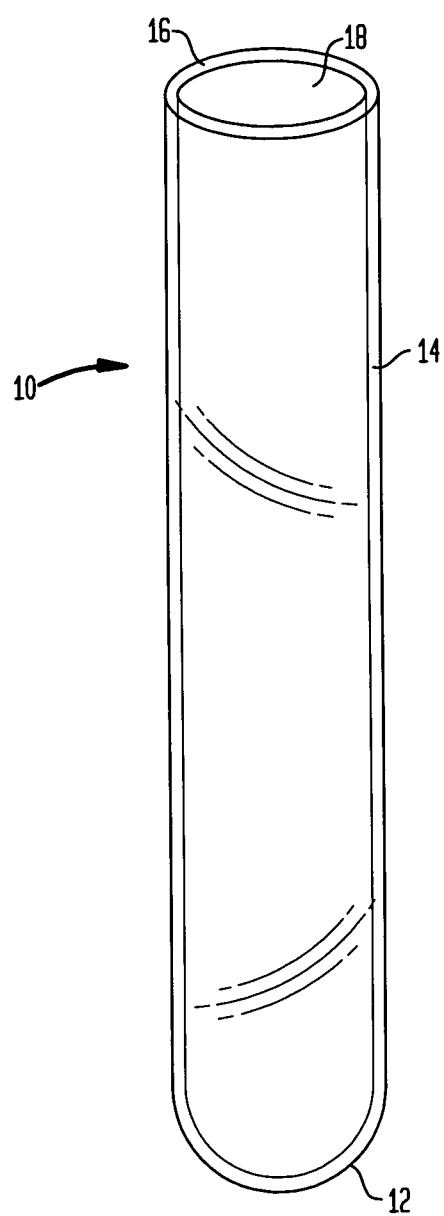
FIG. 1 is a perspective view of a collection tube.

The invention is described in detail below for purposes of illustration only. Modifications within the spirit and scope of the invention, set forth in the appended claims, will be readily apparent to one of skill in the art. Unless defined otherwise, terminology and abbreviations, as used herein, have their ordinary meaning. Following are some exemplary definitions of terms used in this specification and the appended claims.

The phrase "concentrated dispersion," "concentrated nanocomposite dispersion," or like terminology refers to a suspension, dispersion, emulsion, or slurry of exfoliated silicate filler material and a matrix polymer in a liquid carrier medium, where the dispersion is concentrated by removal of a portion of the liquid carrier medium.

"Draw volume", "draw volume loss" and so forth are determined by the draw of deionized water as described herein.

The term "nanocomposite" or "filled polymer nanocomposite" refers to the mixture of substantially exfoliated filler and polymer.

The "oxygen transmission rate," or "OTR," of the coatings used in the invention is measured according to ASTM D-3985-02 or any other suitable protocol using a MOCON® OXTRAN 2/20 module and the following conditions: pressure of 1 atm, a temperature of 23° C., and a relative humidity of 0%.

"Oxygen permeability," as used herein, refers to a property of a material that describes the ease with which oxygen gas transmits through a film made of the material. The composite films of the present invention have an oxygen permeability that is at least 10 times less than that of like films (of the same thickness) which contain no filler.

A "barrier coating composition" or "barrier coating mixture" includes a liquid containing suspended solids, which is used to apply the solids to a substrate. This includes a colloidal dispersion, suspension, emulsion and latex as they are conventionally defined. For example, by "colloidal dispersion or latex" is meant any dispersion or suspension of particles in liquid, the particles being of a size greater than molecular scale, e.g., about 0.001 to about 0.1 micron. An emulsion generally contains particles of about 0.05 to 1.0 microns, in liquid. A "suspension" generally contains particles of greater than 1.0 micron in liquid. A novel aspect of the present invention is that the barrier coating compositions provide a better dispersion of exfoliated mineral fillers in liquid at solids content, e.g., between about 5 to about 20 percent solids as described in more detail below. According to this invention, once the "coating mixture" is dried, it is sometimes referred to as a "dried coating" or a "film".

The term "invisible marker dye" is intended to mean a dye substance which is substantially free of absorption maxima at visible wavelengths and preferably exhibits a single strong absorption peak in the near infrared (NIR) to infrared (IR) region. That is, strong absorption in the region of greater than 700 nm to 1200 nm. Preferably invisible marker dye used in connection with this invention is water soluble and forms a homogeneous mixture with the barrier coating composition of this invention. Optionally, the dye may also be soluble in water miscible solvents such as alcohols, e.g., methanol, ethanol or isopropanol, and the like, ketones such as acetone, methyl ethyl ketone, and the like, esters such as ethyl acetate, n-butyl acetate, and the like. Various other polar water miscible solvents can also be employed, such as dimethyl formamide (DMF), N-methylacetamide (NMAC), dimethyl sulfoxide (DMSO), acetonitrile, and the like. The invisible marker dye is generally characterized in that the barrier coating formed is not visually distinguishable from a like coating formed without an invisible marker dye and the dye is effective to indicate the coating thickness throughout the coating by absorption of light outside of the visible spectrum.

The coatings used invention are transparent in that they freely transmit visible light without imparting color or scattering the light to any substantial degree. In many preferred embodiments, the coated tubes or containers are likewise transparent.

A "like assembly without a nanocomposite barrier film" refers to a substantially identical container assembly without a nanocomposite barrier film.

The liquid carrier medium used for the nanocomposite coatings is aqueous; that is, it is at least 50 percent water, and typically consists essentially of water. Minor amounts of organic solvents may be included in the carrier medium if desired. Suitable solvents may include ethanol, methanol, isopropanol, n-butyl acetate, ethyl acetate, acetone, methyl ethyl ketone, toluene, hexane, other hydrocarbons, and combinations thereof. Preferably the liquid carrier medium is water, free of any other solvents.

The exfoliated silicate filler materials which are dispersed in the liquid carrier medium include layered clay compounds which are made of platelets having a high aspect ratio. "Exfoliation" is defined for layered fillers as the separation of individual layers of the platelet particles; the filler material used in the invention is at least partially exfoliated, and preferably is substantially exfoliated. The aspect ratio is the product of the lateral dimension of a platelet filler particle divided by the thickness of the platelet. The aspect ratio of the filler used in the invention is typically at least 50, and in some cases at least 1,000. In perhaps other cases, from 5,000 up to about 30,000. The thickness of at least some filler particles is below 1 micron, and probably well below 100 nm, preferably less than 10 nm. The exfoliated silicate filler material may include, for example, bentonite, vermiculite, montmorillonite, nontronite, beidellite, volkonskoite, hectorite, saponite, laponite, sauconite, magadiite, kenyaite, ledikite and mixtures thereof. The most preferred fillers are montmorillonite or vermiculite. Suitable montmorillonites are commercially available as SCPX-2973 exfoliated Na montmorillonite slurry, SCPX-2953 exfoliated Na montmorillonite solid, and SCPX-2041 exfoliated Na montmorillonite solid and slurry, all from Southern Clay Products (Gonzales, Tex.).

The silicate filler material may be acid or base pre-treated as is known in the art. The preferred acids for filler pre-treatment are selected from acetic acid, glycine and citric acid, and the preferred bases are selected from ammonium hydroxide, sodium hydroxide and potassium hydroxide. The amount of acid or base employed should be in the amount of from about 10% to about 20% by weight of the dried barrier coating.

The exfoliated filler material is present at between about 5 to about 80% by weight of the total solids of the coating formulations, and preferably from 20 to 50 weight percent of the total solids. The compositions of the present invention, when dried, retain the filler in well-dispersed form, resulting in greatly decreased permeability properties.

The matrix polymers useful in the coating formulations of the present invention are not particularly limited. The matrix resins may include homopolymers and/or copolymers, and are dispersed in the liquid carrier medium as an emulsion or latex. The matrix polymer forms a film in the inventive coatings, in which the platelet particles are dispersed to form a nanocomposite barrier coating. The matrix polymer may be present in amounts of from 5 to 80 weight percent of the total solids in the dispersion, preferably from 30 to 60 or 70 weight percent.

Non-elastomeric polymers, including polyesters, polyamides, chlorinated polymers, polyolefins, polyurethanes, polyethers, polyketones, polycarbonates, acrylics, vinylics, and fluoropolymers are preferred in many cases. Non-elastomeric polymers are generally considered to be those which have a glass transition temperature of greater than 23° C., and/or those with crystallinity above 10%.

Suitable polymers include polyester resins, such as those which are commercially available as Eastek (Eastman Chemical Company, Kingsport Tenn.). The Eastek polymers are sulfopolyesters with a Tg of from about 30 to 35° C.

Preferred resins include polymers selected generally from among many classes. The selected polymers may be curable polymers, partially cured polymers, or uncured polymers, and are dispersible in water.

The invisible marker dye may be a water soluble infrared (IR) sensitive organic or inorganic or hybrid organic-inorganic compounds. The dye having a strong absorption at a narrow wavelength is particularly preferred. Even more preferably a dye suitable for this invention is having strong absorption in the near infrared (NIR) region of the electromagnetic spectrum, i.e., in the region of 700 nm to 1200 nm, more preferably over the range 750 nm to 1000 nm, and most preferably over the range 750 nm to 850 nm. As already noted above, water soluble invisible marker dye is preferred, however, a dye soluble in other water miscible solvents may also be suitable in this invention.

Examples of such NIR dyes are disclosed in JOEM Handbook 2 Absorption Spectra of Dyes for Diode Lasers, Matsuoka, Ky., bunshin Shuppan, 1990 and Chapter 2, 2.3 of Development and Market Trend of Functional Coloring Materials in 1990's, CMC Editorial Department, CMC, 1990, such as polymethine type coloring material, a phthalocyanine type coloring material, a dithiol metallic complex salt type coloring material, an anthraquinone type coloring material, a triphenylmethane type coloring material, an azo type dispersion dye, and an intermolecular CT coloring material. The representative examples include N-[4-[5-(4-dimethylamino-2-methylphenyl)-2,4-pentadienylidene]-3-methyl-2-,5-cyclohexadiene-1-ylidene]-N,N-dimethylammonium acetate, N-[4-[5-(4-dimethylaminophenyl)-3-phenyl-2-pentene-1-ylidene]-2,5-cyc-lohexadiene-1-ylidene]-N,N-dimethylammonium perchlorate, bis (dichlorobenzene-1,2-dithiol)nickel(2:1)tetrabutyl-ammonium and polyvinylcarbazol-2,3-dicyano-5-nitro-1,4-naphthoquinone complex. Some specific commercial products that may be employed include Pro-jet 830NP, a modified copper phthalocyanine from Avecia of Blackley, Lancashire in the U.K., and ADS 830A, an infra-red absorbing dye from American Dye Source Inc. of Montreal, Quebec, Canada. Other examples of NIR dyes include 2,4,5,7-tetranitrofluorenone or (2,4,7-trinitrofluorenylidene)-malononitrile, which are described in U.S. Pat. No. 7,323,889, which is incorporated herein by reference in its entirety.

Water soluble NIR dyes are particularly preferred. Some specific water soluble commercial products that may be employed include SDA 1910 (Abs. Max. 910 nm), SDA 6122 (Abs. Max. 868 nm), SDA 1868 (Abs. Max. 868 nm), SDA 8700 (Abs. Max. 844 nm), SDA 8208 (Abs. Max. 824 nm), SDB 4927 (Abs. Max. 822 nm), SDA 9362 (Abs. Max. 820 nm) SDA 7563 (Abs. Max. 819 nm), SDA 9158 (Abs. Max. 808 nm), SDA 1842 (Abs. Max. 807 nm), SDB 8662 (Abs. Max. 784 nm), SDA 1372 (Abs. Max. 782 nm) and SDD5712 (Abs. Max. 781 nm) from HW Sands Corp. SDA 8700 and SDB 4927 are particularly preferred.

SDB-4927 is an infrared-absorbing dye, namely 2-(2-(2-chloro-3-(2-(1,3-dihydro-1,1-dimethyl-3-(4-sulfobutyl)-2H-benz[e]indol-2-ylidene)ethylidene)-1-cyclohexene-1-yl) ethenyl)-1,1-dimethyl-3-(4-sulfobutyl)-1H-benz[e] indolium, inner salt, free acid having CAS No. [162411-28-1], available from H. W. Sands Corp., Jupiter, Fla. It has absorption maximum: 822 nanometers (in methanol), extinction coefficient 240,000 L/(mol·cm), melting point: 253-255 degrees Celsius (decomposition), solubility: 30 mg/mL (in methanol), appearance: dark green powder, molecular weight of about 827 grams per mole, and is synonomous with 2-[2-[2-(Chloro-3-[2-(1,3-dihydro-1,1-dimethyl-3-(4-sulfobutyl)-2H-benz[e]indol-2-ylidene)ethylidene]-1-cyclohexen-1-yl]ethenyl]-1,1-dimethyl-3-(4-sulfobutyl-1H-benz[e]indolium, inner salt, free acid, CAS No: 162411-28-1.

SDA-5802 is an infrared-absorbing dye, 2-[2-[2-(2-pyrimidinothio)-3-[2-(1,3-dihydro-1,1-dimethyl-3-(4-sulfobutyl)-2H-benz[e]indol-2-ylidene)]ethylidene-1-cyclo penten-1-yl]ethenyl]-1,1 dimethyl-3-(4-sulfobutyl)-1H-benz[e] indolium, inner salt, sodium salt, having molecular formula $C_{41}H_{47}N_4NaO_6S_3$ and molecular weight of about 811 grams per 30 mole, available from H.W. Sands Corp., Jupiter, Fla. See U.S. Pat. No. 6,881,526 and United States Application Publication No. US 2005/0214659.

It is particularly preferred that the invisible marker dye used in connection with this invention has strong single absorption peak in the NIR or IR region, preferably in the NIR region of the electromagnetic spectrum. More preferably, the invisible marker dye of this invention is substantially free of color thus imparting no color to the coating compositions of this invention. It is even more preferred that the invisible marker dye of this invention forms a transparent film when used with the coating compositions of this invention. Generally, the dye is present in the dispersion in an amount of at least 5 mg/liter, such as in an amount of at least 5 mg/liter and up to 100 mg/liter. In some cases, the dye is present in the dispersion in an amount of at least 10 mg/liter and up to 50 mg/liter.

The barrier coating formulations of the invention may optionally employ at least one or more than one suitable surfactant to reduce surface tension, and aid in dispersion. Surfactants include materials otherwise known as wetting agents, anti-foaming agents, emulsifiers, dispersing agents, leveling agents etc. Surfactants can be anionic, cationic and nonionic, and many surfactants of each type are available commercially. A suitable surfactant for inclusion in these compositions possesses a critical micelle concentration sufficiently low to ensure a dried barrier coating uncompromised by residual surfactant. In the event of an unfavorable interaction of the anionic emulsifier present in the latex dispersion, additional ionic additives should be kept to a minimum. This variable is eliminated where the surfactant or emulsifier is non-ionic. Increase in ionic concentration of the compositions, such as by the addition of a base to adjust pH, e.g., KOH, NH$_4$OH and NaOH, may cause agglomeration of the filler, which adversely affects permeability reduction.

Desirable surfactants may include SURFYNOL® PSA 336 (Air Products, Inc.), SILWET® L-77 (OSI Specialties, Inc.), and ZONYL® FSP and 8952 (DuPont Performance Chemicals and Intermediates). The amount and number of surfactants added to the coating composition will depend on the particular surfactant(s) selected, but should be limited to the minimum amount of surfactant that is necessary to achieve wetting of the substrate while not compromising the performance of the dried barrier coating. For example, typical surfactant amounts can be less than or equal to about 15% by weight of the dried barrier coating.

The dispersions may also include additional additives such as biocides, colloidal dispersants, anti-foaming agents, dispersing agents, wetting agents, leveling agents, and thickeners. Other optional components of the coating mixture include conventional agents to adjust pH, such as bases, e.g., NH$_4$OH, NaOH or KOH; or acids, e.g., acetic acid, citric acid or glycine provided that care is taken to avoid agglomeration, as discussed above.

As noted above, the dispersions of the invention are produced according to a method whereby the silicate filler and polymer component are dispersed in the liquid medium at a given concentration, and this initial dispersion is subsequently condensed by selectively removing a portion of the liquid carrier medium. In the condensing step, a portion of the liquid carrier medium is selectively removed to increase the solids content of the dispersion. Suitable removal methods include evaporation, distillation, and the like. The liquid may be evaporated off by heating; preferably at a temperature of from about 80° C. to about 100° C. for about 70 to about 100 minutes while stirring until about 1% to about 30% of the liquid carrier evaporates.

The dispersions are typically condensed such that the solids content of the dispersion increases by at least 5%, i.e., has a solids content of at least 1.05 times that of the initial, unconcentrated dispersion. More preferably, enough liquid is removed such that the solids content increases by at least 25% or at least 50%. The concentrated dispersion generally includes from about 5 to 25 weight percent solids, and preferably from about 7 to 15 weight percent solids. Before it is concentrated, the dispersion typically includes from about 3 to 7 weight percent solids. It is unexpected that the dispersion may be concentrated by evaporation without causing the formulation to gel. For example, many silicate filler materials, such as montmorrillonite, form gels at relatively low solids content, and the solids content of the silicate component often limits the final solids content of the barrier coating.

The invisible marker dye is then added to the concentrated dispersion. The dye in desirable amount is dissolved in water and if desired further diluted to the desirable concentration. Then the aqueous dye solution is added to the concentrated dispersion while stirring in order to obtain well dispersed dye containing concentrated dispersion.

The coating formulations of the invention are generally applied to a tube and dried to form a low permeability barrier coating as described hereinafter. The coating films that are produced provide an excellent gas barrier. Generally, the coatings produced according to the invention exhibit a reduction in oxygen permeability of at least 100-fold as compared to a similar barrier coating which does not include silicate filler material. More preferably, the barrier coating produced according to the present invention exhibits at least a 200-fold, at least a 400-fold, and even more than 900-fold reduction in gas permeability as compared to a barrier coating which does not include the silicate filler material. Suitable permeability values for the coating may be less than 0.02 cc-mm/m$^2$-day-atm, or less than 0.01 cc-mm/m$^2$-day-atm. It should further be noted that addition of dye solution to concentrated dispersion does not compromises the barrier properties of the resulting dye containing dispersion, which aspect becomes even more apparent from the specific Examples that are described in more detail below.

Furthermore, it has been surprisingly discovered according to the present invention that coatings which were made from concentrated dispersions, i.e. condensed, exhibit superior oxygen barrier properties as compared with a like coating (same composition and thickness) which is prepared from a like dispersion that did not undergo selective removal of the liquid carrier medium, i.e., a dispersion that is prepared by adding the filler material at higher solids content in polymer latex, without subjecting the dispersion to substantial evaporation or other liquid removal. Remarkably, the barrier properties of the invention are superior to uncondensed formulations, even where the solids content and composition are the same. As compared to films formed from dispersions which did not undergo an evaporation step, the inventive coatings exhibit permeability values that are at least 10 percent, and preferably at least 20 percent lower.

In addition to reduced gas permeability, the high solids coating formulation produced in accordance with the present invention provides a product with reduced drying times, higher viscosity and thus thicker dip coated samples in a single step, better suspension stability, reduced shipping costs, thicker spray coatings without dripping, reduced penetration of coating into substrate porosity and defects, and thicker coating in continuous film and paper coating applications.

Another non-limiting advantage of this invention is that the use of an invisible marker dye in coatings compositions of this invention provides transparent high barrier coatings at thicknesses from 1-10 microns that include an NIR or IR dye that enables rapid measurement of coating thickness and uniformity. Preferably, the invisible marker dye of this invention imparts no observable color or appearance change, and thus can also function as a security marker to determine if a product has used barrier coatings of this invention, and how much has been used.

Additionally, the nanocomposites can be coated onto a tube and the thickness of coating may be measured at a fixed wavelength at which the dye exhibits a strong absorption. Thus, in accordance with the method of this invention in a given coating system, preferred dye in the coating produces an absorption which increases with thickness over the probable thickness range of coating in a uniform manner. It is even more preferred that the increase be reproducible and capable of representing thickness as a function of intensity of absorption. Most preferably, the relationship between the thickness of the coating and the absorption intensity is linear. It is further evident from the Examples that follow, such coating compositions containing an invisible marker dye can be readily formed for the purpose of controlling coating thickness as well as coverage.

In accordance with the present invention there is provided an evacuated container assembly suitable for use in connection with blood collection generally including: (a) a container member formed of a first polymeric material and having a closed bottom, an open top and a sidewall therebetween thereby defining a collection cavity with an inner surface; (b) a nanocomposite barrier coating disposed on the container member having a thickness of up to about 30 microns and being derived from an aqueous dispersion including (i) a dispersed barrier matrix polymer; and (ii) a substantially exfoliated silicate filler having an aspect ratio of more than 50; and (c) a sealing member disposed in the opening operative to hermetically seal the cavity; wherein the cavity is evacuated and maintains a pressure below atmospheric pressure and exhibits a draw volume loss lower than that of a like assembly without a nanocomposite barrier film by a factor of at least 1.5. A typical construction is shown schematically in FIGS. 1-4.

Figure 2:
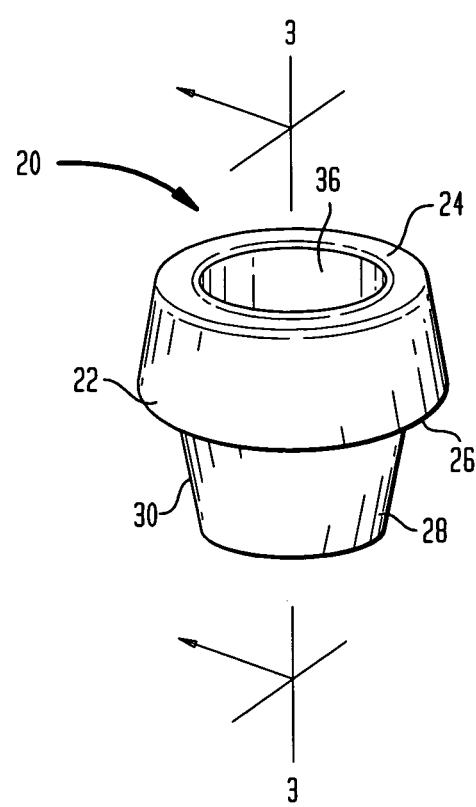
FIGS. 2 and 3 illustrate a puncturable closure for the tube of FIG. 1, with FIG. 3 showing the cross-section at line 3-3.
Figure 3:
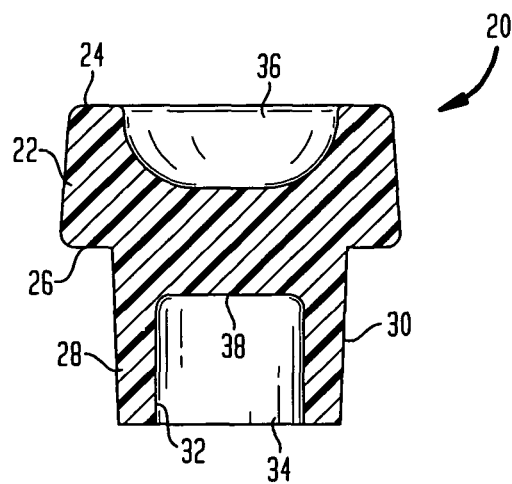
Figure 4:
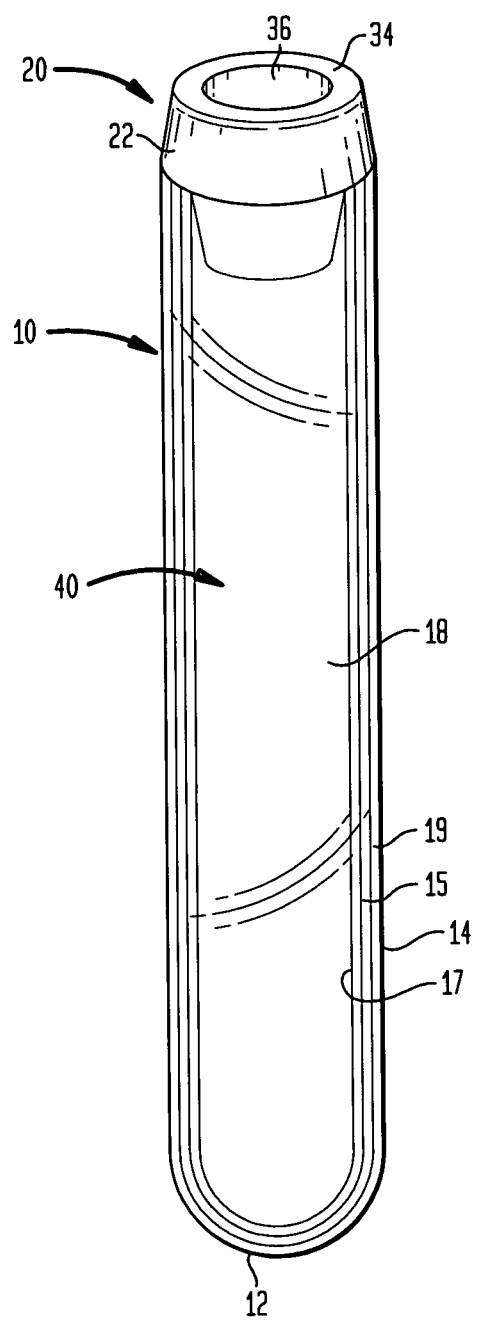
FIG. 4 is a perspective view of a blood collection assembly of the invention including the tube and closure of FIGS. 1-3.

FIGS. 1-4 illustrate a blood collection tube and closure according to an embodiment of the invention. In FIG. 1 it is seen tube 10 has bottom wall portion 12 and sidewall portion 14 continuous therewith. (The multilayer coating of sidewall portion 14 is not shown in FIG. 1.) Sidewall portion 14 has a top edge 16 and defines an open end 18. A straight sidewall portion 14 is shown for the tube 10, but complex sidewall shapes, for other containers, are also possible. FIGS. 2-3 illustrate a useful closure or sealing member 20 for open end 18 of FIG. 1. Various other configurations for the closure, of any suitable materials, are possible. Closure 20 includes an annular upper portion 22 having a top wall 24. Upper portion 22 has a lower wall or lip 26, which extends over top edge 16 of tube 10 when the closure is in the tube. Stopper 20 also includes a lower annular portion or skirt 28 having an outside wall 30 which forms an interference fit with the inside wall surface of tube 10 to maintain the stopper in the tube. Skirt 28 also has an inside wall surface 32, which defines a well 34. Top wall 24 defines a closure cap cavity 36. A septum 38 separates well 34 and cavity 36 for penetration by a cannula when the tube assembly is ready for use. FIG. 4 illustrates the tube and stopper assembly ready for drawing a blood sample into enclosed interior space or collection cavity 40.

In FIG. 4, tube 10 is shown coated with a barrier layer 15 in between an adhesive layer 17 and a topcoat 19. Tube 10 is typically a polypropylene or polyethylene terephthalate tube and barrier coating 15 is a nanocomposite barrier coating as described herein. Adhesive layer 17 may be a urethane resin such as for example Neorez R600. Topcoat 19 may be a vinyl acrylic resin such as for example Flexbond 325 or a resin such as DigiGuard™ gloss 110. Alternatively, topcoat layer 19 may be a polymer, or blend of monomers and/or macromers based on acrylate, di-acrylate, multifunctional acrylate, or urethane acrylate resins or other suitable resins which allow for radiation curing using for example UV radiation or heat curing. Topcoat layer 19 protects the barrier layer as well as provides a superior appearance to the product.

Figure 4A:
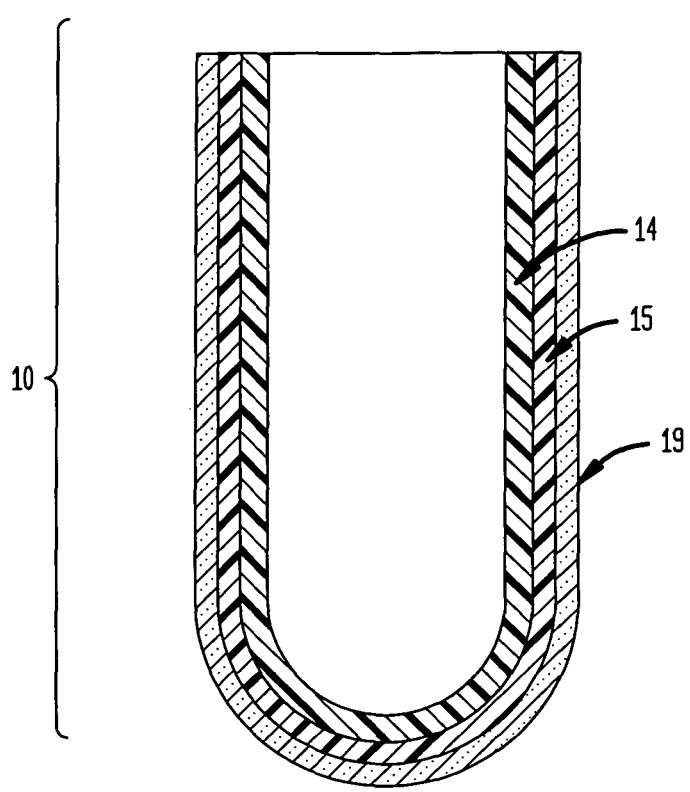
FIG. 4A is a detail showing a three layer construction of an evacuated tube.
Figure 4B:
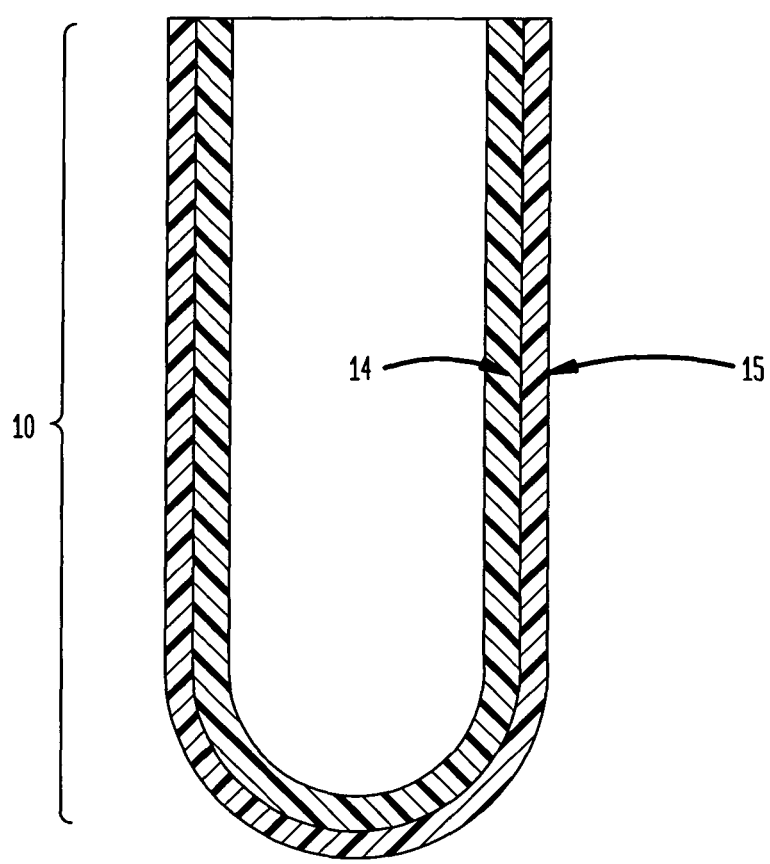
FIG. 4B is a detail illustrating a two layer construction of an evacuated tube.
Figure 4C:
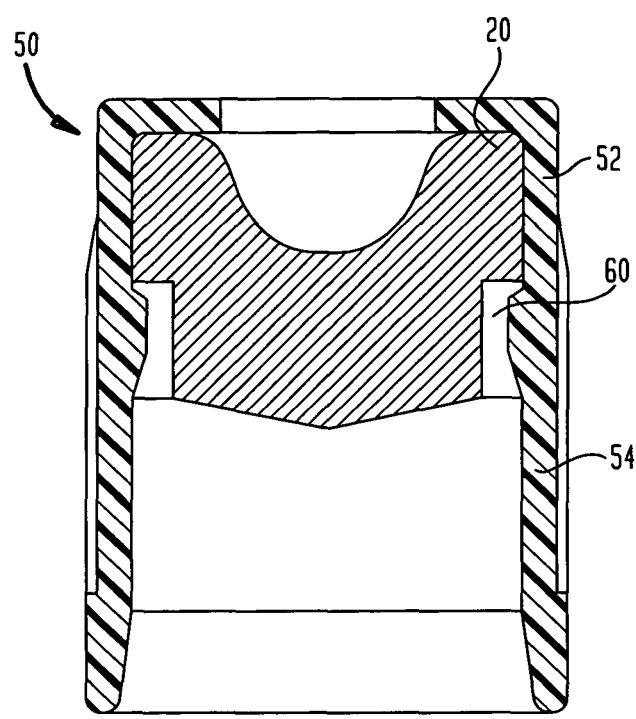
FIG. 4C is a detail showing a stopper and shield assembly which may be used in accordance with the present invention.

FIG. 4A further illustrates the construction of tube 10. In the embodiment shown in FIG. 4A, tube 10 includes a container member 14, a barrier layer 15, as well as a topcoat 19. Likewise, FIG. 4B shows a construction of tube 10 including a container 14 as well as a barrier coating 15. FIG. 4C illustrates a stopper and shield assembly 50 including a stopper 20 as well as a shield 52. Shield 52 has an elongated shield portion 54, while stopper 20 is configured to receive tube 10 at rim 60. Further details relating to a suitable stopper and shield assembly is shown in U.S. Pat. No. 6,602,206 to Niermann et al., the disclosure of which is incorporated herein by reference in its entirety.

It will be appreciated from the foregoing that the tubes useful in connection with the invention are distinguished from the pre-forms used for blow molding in that they do not have threads. Moreover, the invention provides advantages over uncoated tubes in that the defect resulting from the injection molding "gate" typical at the bottom of the tube is covered by the barrier coatings noted above.

Further details concerning the manufacture and composition of tube 10 and closure 20 as well as evacuation levels, anticoagulants and so forth are found in the following references, the disclosures of which is incorporated herein by reference: United States Patent Application Publication No. US 2005/0037165 A1, published Feb. 17, 2005, entitled "Multilayer Containers and Process for Forming Multilayer Containers", of Ahern et al.; U.S. Pat. No. 6,749,078, issued Jun. 15, 2004, entitled "Collection Assembly", to Iskra; U.S. Pat. No. 6,651,835, issued Nov. 25, 2003, entitled "Collection Container Assembly", to Iskra; U.S. Pat. No. 6,354,452, issued Mar. 12, 2002, entitled "Collection Container Assembly", to DeSalvo et al.; U.S. Pat. No. 5,871,700, issued Feb. 16, 1999, entitled "Holding Device With a Cylindrical Container and Blood Sampling Tube With Such a Holding Device", to Konrad; and U.S. Pat. No. 4,830,217, issued May 16, 1989, entitled "Body Fluid Sample Collection Tube Assembly", to Dufresne et al.

Evacuated Container Assembly Examples

The following materials and methods were used to fabricate and test evacuated collection container assemblies of the invention and like assemblies without a barrier coating:

Materials 1) 13×75 mm Polypropylene (PP) tubes with internal volume=5.8424 mL.

2) 13×75 mm Polyethylene Terephthalate (PET) tubes with internal volume=5.988 mL.

3) Coating
   a) Barrier Coating Material: Nanolok® PT MM 3580
   b) Primer Material: NeoRez® R600
   c) Topcoat Material: Flexbond® 325

4) 13 mm Citrate Hemogard Closures (stopper and shield), lubed with SF-96-100

5) Ball bearings—Laboratory Stock, size (quantity): ⅟₁₆" (1), ¼" (1), ⁵⁄₁₆"
   (1). Total Ball Bearing Volume=0.3980 mL.

Methods
1) PP tubes were injection molded.
2) PP tubes were coated with a three-dip coating process as follows:

Dip 1: Primer Layer

The primer layer is made by diluting NeoRez® R600 (Neoresins) to 25% solids. The tube is dipped into the solution and pulled out immediately. The tube is held for 15 seconds and then turned over and dried using a heat gun at 50° C. setting for approximately 30 seconds.

| | |
|---|---|
| Solution solids: | 25% |
| Dip process: | 1 dip |
| Drying time: | 15 seconds, 30 seconds |
| Drying conditions: | room temperature, 50° C. heat gun |
| Orientation of tube: | top up, top down |

Dip 2: Barrier Layer

The barrier layer is Nanolok® PT MM 3580 (nanocomposite of polyester polymer with montmorrillonite filler), preferably between 8-9% solids. Slow stirring of the formulation is recommended. The primed tube is dipped top up into the formulation. The tube is immediately removed and shaken for 45 seconds to remove dripping. After 45 seconds, the tube is turned top down and dried at room temperature for 15 minutes. Drying can be accelerated with forced air but was not for these tubes.

| | |
|---|---|
| Solution solids: | 8-9% |
| Dip process: | 1 dip |
| Drying time: | 45 seconds, 15 minutes |
| Drying conditions: | room temperature, room temperature (accelerated possible) |
| Orientation of tube: | top up, top down |

Dip 3: Top Coat Layer

The topcoat layer is made by diluting Flexbond® 325 (Air Products) to 25% solids. The tube is dipped into the solution and pulled out immediately. The tube is held for 15 seconds top up and then turned over and dried a heat gun at 50° C. setting for 30 seconds.

| | |
|---|---|
| Solution solids: | 25% |
| Dip process: | 1 dip |
| Drying time: | 15 seconds, 30 seconds |
| Drying conditions: | room temperature, 50° C. heat gun |
| Orientation of tube: | top up, top down |

3) Each coated tube was filled with 0.3980 mL of ball bearings, to represent 0.40 mL of DI $H_2O$ present in a realized citrate tube product. Using ball bearings instead of $H_2O$ eliminates the effect of moisture transmission on draw volume retention measurements.
4) Tubes evacuated with an evacuation pressure=215.335 mmHg and placed into storage immediately following evacuation. Storage Conditions: 25° C., 50% RH; 40° C., 50% RH
5) Tubes were removed from storage at given time points and tested for draw volume.
   a) Time points: Day 0, 1, 3, 6, 13, 20, 30, 62, 91, 122
6) Draw Volume Test at lab conditions (20-25° C.):
   a) Mass empty tube assembly
   b) Draw DI $H_2O$ into tube using Draw Volume machine, R&DPAS-010
   c) Pressure set to 760 mmHg
   d) Luer-Lok Blood Transfer Device transfers water for 15 seconds Equipment
1) Gravimetric Volume Draw Method: The equipment used was an analytical balance to determine the draw volume by weight. The analytical balance was a Bohdan Model BA-200 by Mettler Toledo (serial #1322470389).

Data Analysis
1) The rate of draw volume loss over time was calculated via a linear regression of the data.
2) To obtain a proper regression fit, the data window was shifted to target only steady-state air transmission across three months.
3) Polypropylene is known to out-gas (release dissolved air from within the polymer matrix into the tube interior once under vacuum) quicker than PET, thus the starting point of data analysis was delayed until the PET control reached a steady-state (Day 30 and beyond).
4) Final time points incorporated into regression analysis: Day 30, 60, 90, 120. Total data points per regression=80.
5) All statistical analysis performed in MiniTab. Each data point was assessed against the estimated regression fit value. Strong outliers were identified via Cook's Distance analysis, demonstrating an unbalanced weight in the regression constants.
6) If any data point showed elevated Cook's Distance relative to the rest of the group, it was eliminated from the regression analysis.
7) The slope of each refined linear regression was used as an estimate for average draw volume loss over time. The draw volume loss acts as a point of comparison between different tube resin and coating systems.

Results

Polypropylene tubes coated with a barrier coating outperform PET tubes in draw volume testing, showing an improvement of 1.72× at 25° C. The coating performance is influenced by increases in temperature, to a greater degree than native PET. At 40° C., coated PP showed 0.92× improvement relative to PET control.

TABLE 1

Draw Volume Loss Data of Coated Polypropylene Tubes vs. PET Control

| | Draw Volume Loss Rate [μL/day] | Standard Error [μL/day] | Improvement Ratio [/PET Control] |
|---|---|---|---|
| Barrier Coated PP Tube - 25° C. | 1.24 | 0.13 | 1.72× |
| PET Control Tube - 25° C. | 2.13 | 0.06 | 1.00× |
| Barrier Coated PP Tube - 40° C. | 3.23 | 0.27 | 0.92× |
| PET Control Tube - 40° C. | 2.97 | 0.06 | 1.00× |
| PP Reference - 25° C. | 53.3 | — | 0.04× |
| TNT Ref - 25° C.[†] | 2.06 | — | — |
| TNT Ref - 25° C.[†] | 1.78 | — | — |

[†]Testing included liquid-filled tubes, which enhance realized air barrier performance; that refers to a PET/PP structure.

Figure 5:
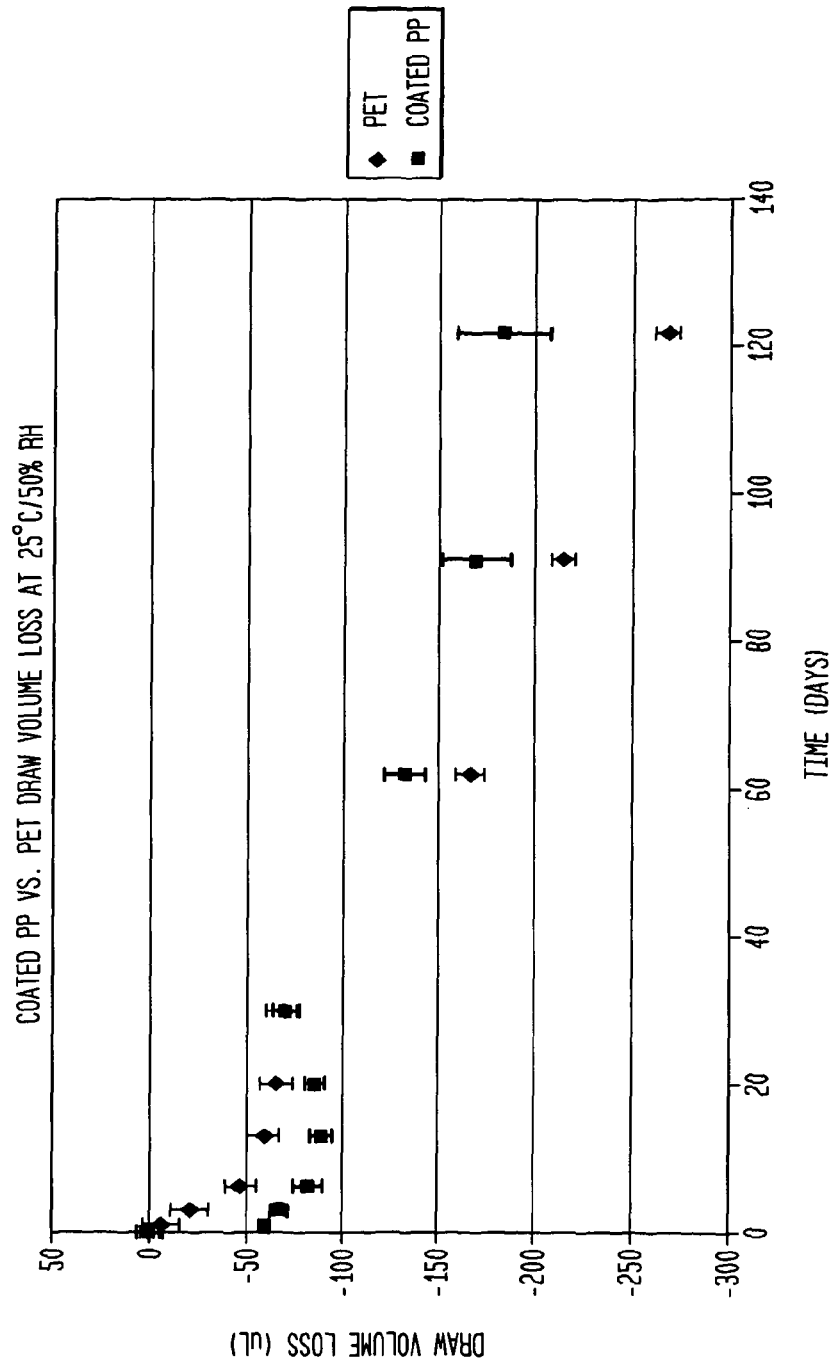
FIG. 5 is plot of draw volume loss of barrier coated PP tubes with PET Control at 25° C.
Figure 6:
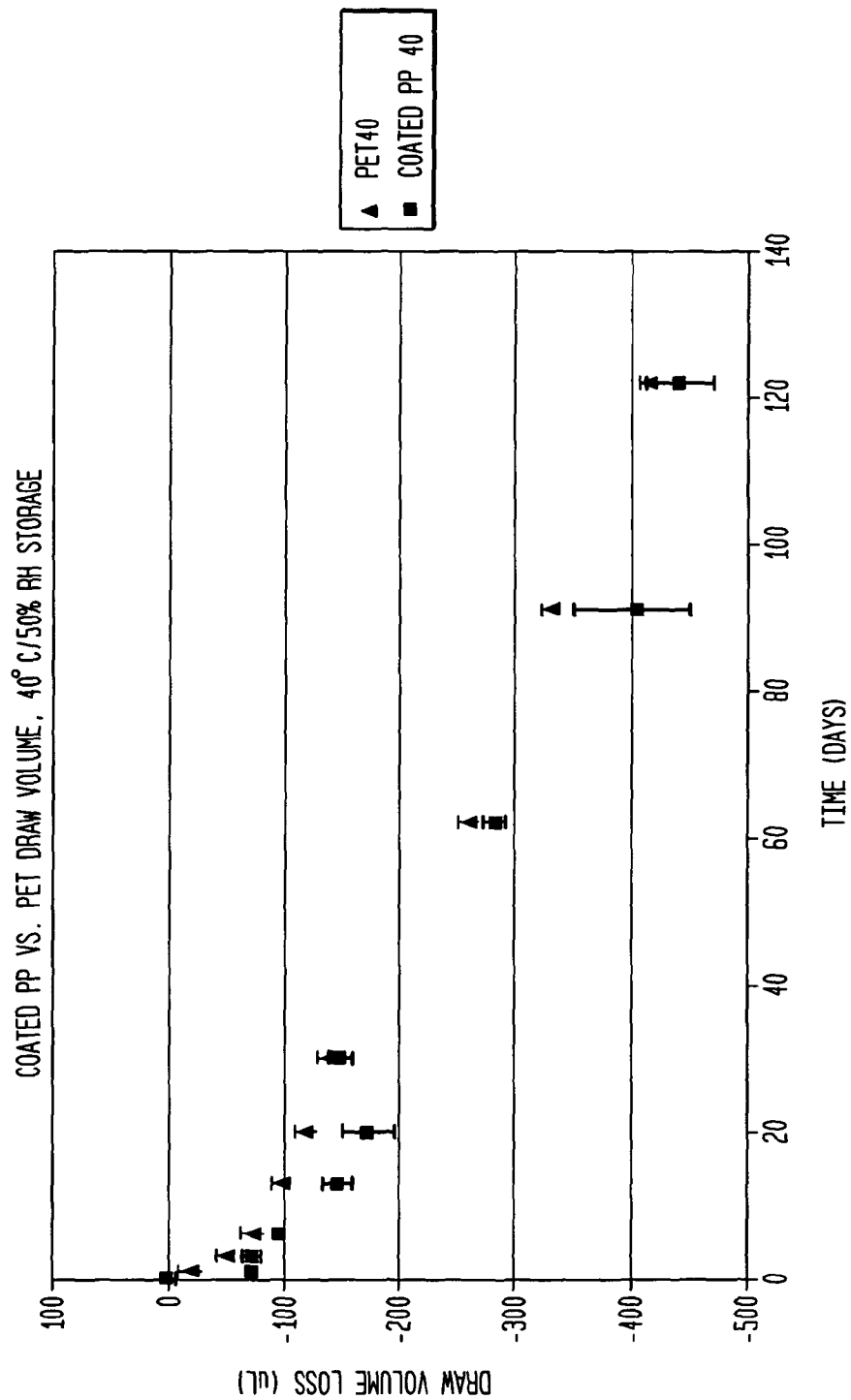
FIG. 6 is a plot of draw volume loss of barrier coated PP tubes with PET Control at 40° C.

Draw volume loss over time is presented graphically in FIGS. 5 and 6 and thickness data appears in Table 2, below. It is appreciated from Tables 1, 2 as well as FIGS. 5 and 6 that the barrier coating greatly reduces draw volume loss, over 40-fold even though the film is only 4-6 microns thick.

TABLE 2

Coating Thickness Tubes*

| | Target Thickness [μm] | Optical Profilimetry [μm] (No. of Tubes) | Filmetrics [μm] (No. of Tubes) |
|---|---|---|---|
| Glass - Barrier Coat | 4-6 | 4.5-6.0 (2) | 5.5-6.2 (2) |
| PET - Barrier Coat | 4-6 | 5.5-8.0 (2) | 6.1-6.6 (4) |
| PP - Barrier Coat | 4-6 | 10-12 (2) | 6.3 (1) |
| PP - Primer Coat | — | — | 10-13.4 (2) |
| PP - Primer and Barrier Coats | 4-6 (Barrier) | — | 5.8-6.4 (2)‡ |

*All measurements taken in the middle of the tube. Coating thickness has potential variability within a given tube due to the dip process.
‡Measurement could be artifact of Filmetrics technique.

Instead of using an adhesive layer, tube 10 may be plasma treated and the barrier layer 15 directly applied to tube 10 prior to topcoating. To this end, a three-dimensional Dyne-A-®Flame™ (DF200) plasma treater from Enercon Industries Corporation was evaluated. The Dyne-A-Flame™ treater uses a sophisticated combustion control system and a high-velocity Power Flame burner to form precisely contoured treatment flames. Intense treatment increases the surface energy and surface tension of the treated objects.

A combination of flammable gas and air creates a plasma field forming an intense blue film such that brief exposure of the flame to the surface of the sample affect the distribution and density of electrons on the sample surface and polarizes surface molecules through oxidation. Surface energy on the sample increases promoting better adhesion of coatings. Flame plasma treatment generates more heat than other treatment methods, but creates greater surface energies with a longer shelf life.

Different techniques were tried for flame treatment on PP tubes. They are enumerated in Table 3. The different experimental conditions are reported in Tables 4 and 5.

TABLE 3

Different types of plasma treatment on PP tubes prior to barrier coating

| Sample Set | Package Label | Enercon Treatment Type | Head/Burner Type | Head/Sample Orientation | Area Treated | Passes |
|---|---|---|---|---|---|---|
| 1 | HP Head Perpendicular | Dyne-A-Mite HP | Deluxe Wide Tip | Perpendicular | ⅓ circumference | 1 |
| 2 | HP 1 pass | Dyne-A-Mite HP | Deluxe Wide Tip | Parallel | Spotty | 1 |
| 3 | HP 2 pass | Dyne-A-Mite HP | Deluxe Wide Tip | Parallel | Spotty | 2 |
| 4 | VCP 1 pass | Dyne-A-Mite VCP | Standard | — | — | 1 |
| 5 | VCP 2 pass | Dyne-A-Mite VCP | Standard | — | — | 2 |
| 6 | Flame | Dyne-A-Flame | 24 Series | — | — | — |

In Table 3, HP refers to a process where blown-arc air plasma is formed by blowing atmospheric air past two high-voltage powered electrodes and is sometimes referred to as corona treatment. The electrical discharge positively charges the ion particles surrounding it. Through direct contact, these particles positively charge the treated area of the object's surface. This makes the surface more receptive to any applied substance such as inks. Air plasma is a popular surface-treatment technology because it is effective, easy to use and inexpensive to operate.

Dyne-A-Flame™ refers to Enercon's standard flame treatment where a plasma field is formed when flammable gas and air are combined and combusted to form an intense blue flame. Brief exposure to the energized particles within the flame affects the distribution and density of electrons on the substrate's surface and polarizes surface molecules through oxidation. This method also deposits other functional chemical groups that further promote ink wetting and adhesion. FlamePlasma treatment generates more heat than other treatment methods, but creates greater surface energies with a longer shelf life. Flame treatment is commonly used to process injection and blow-molded products because of the thickness, size, and shape of the parts.

The Dyne-A-Mite VCP method blends air (O2, N2) with other gases that deposit various chemical groups on the substrate surface to improve its surface energy. Variable chemistry plasma treatment is essentially an etching and functionalizing process that provides different surface characteristics depending on the gas chemistry employed.

TABLE 4

Different parameters during and after treatment

| Sample Set | Heads to Cover Length | Treated Width | Line Speed FPM | Initial Dyne Level | Final Dyne Level |
|---|---|---|---|---|---|
| 1 | 1 | — | 75 | 30 | 70 |
| 2 | 2 | — | 75 | 30 | — |
| 3 | 2 | — | 75 | 30 | — |
| 4 | 2 | 1.75 | 75 | 30 | 70 |
| 5 | 2 | 1.75 | 10 | 30 | 70 |
| 6 | — | — | 75 | 30 | 70-72 |

TABLE 5

Experimental parameters used on PP tubes

| | |
|---|---|
| Gap between the burner and the test tubes | 1.5" |
| Distance between tubes | 1.5" |
| Speed | 75 fpm |
| Air/gas ration | 10:1 |
| Air flow | 200 L/min |
| Gas flow | 20 L/min |

Figure 7:
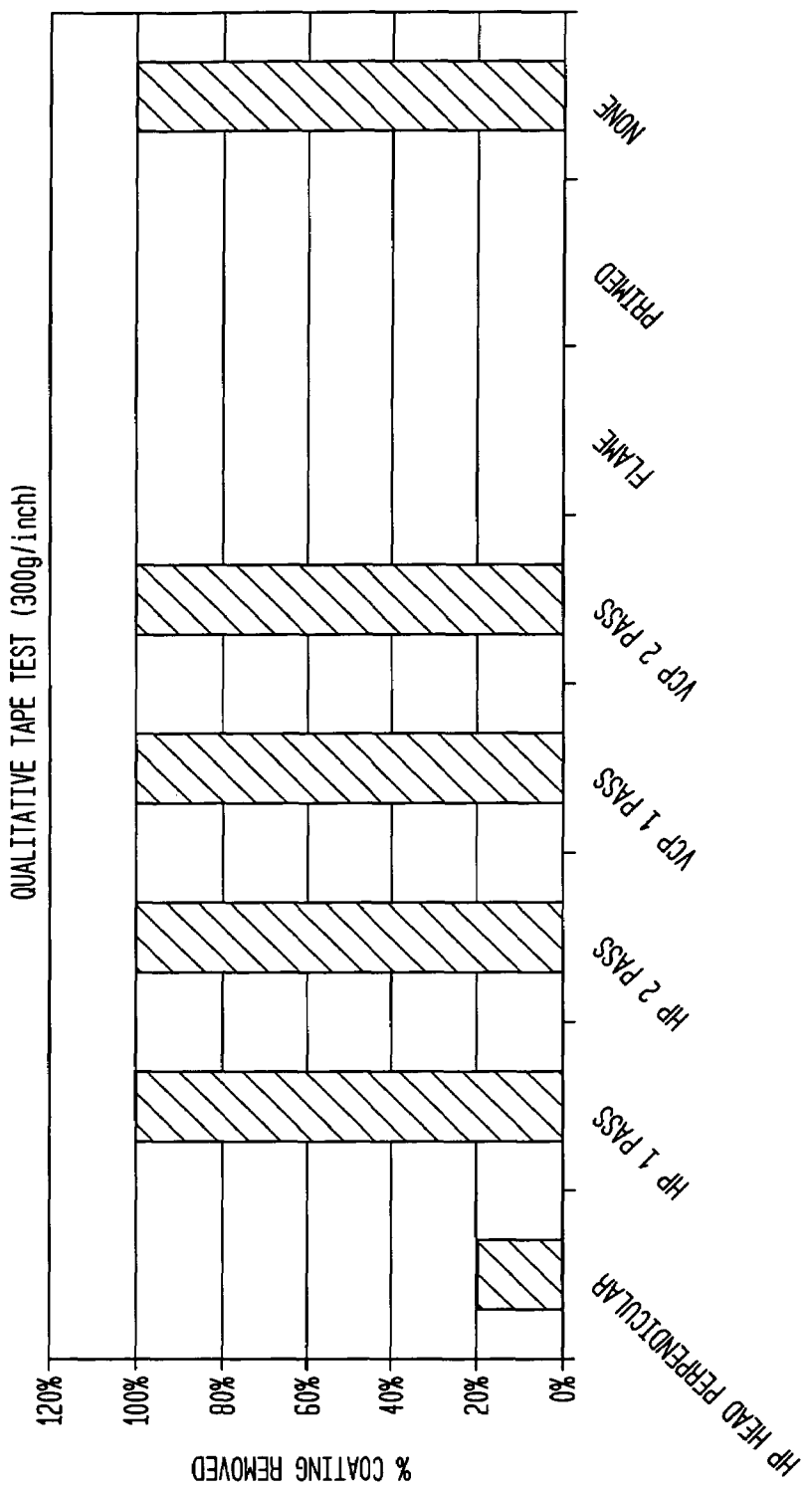
FIG. 7 is a plot of qualitative tape test results of coating on flame plasma treated PP tubes.

Plasma treated polypropylene tubes were coated with Nanolok® PT MM 3580 and tested the basic adhesion with 610 standardized tape (300 g/in peel strength). The results are presented in FIG. 7. The treated tubes were compared with primed and untreated tubes as well. The tubes that showed the best results were the primed control tube and the flame treated tube. The HP head perpendicular tube had moderate adhesion with about 20% loss from the tape test.

BARRIER COATING EXAMPLES

In the following examples, nanocomposite barrier coating compositions suitable for use in collection container assemblies of the class described above are prepared and applied to polyester substrates and glass plates and then are tested for oxygen transmission rate. The nanocomposite barrier coating films are prepared in an aqueous medium with a polyester resin (Eastek 1000, Eastman, 30% polymer solids) as the polymer matrix and montmorrillonite (SCPX-2973, SCPX-2953, or SCPX-2041) as the exfoliated silicate filler.

While the permeabilities of films are representative, it will be appreciated by one of skill in the art that the permeabilities of the stopper or stopper employed is likewise a salient feature of the evacuated tubes produced. If one coated the stopper with a suitable nanocomposite, barrier properties are still further improved. When you have materials in series (as with the coating on the PP) then we use the equation 1/total permeation rate=1/permeation rate of layer 1+1/permeation rate of layer 2, where the permeation rate of the individual layers is the rate they would have if the other layer had not been present. If it is desired to coat the stopper, it may be preferable to use an elastomeric resin/exfoliated mineral nanocomposite as described, for example, in U.S. Pat. No. 6,087,016 to Feeney et al., the disclosure of which is incorporated herein by reference.

Experimental Procedures

Oxygen Transmission Rate (OTR) Testing

Films and coated substrates are tested for oxygen transmission rate using a Mocon® OXTRAN 2/20 or 2/60 module at 23° C., 0% RH, and 1 atm. The samples are loaded onto the modules and conditioned for 2 hours prior to testing for oxygen. Once equilibrium is reached, an OTR is reported in units of cc/m² day atm.

Thickness Measurements

All thickness calculations are based on the weight of the coating, and an assumed density. For the purposes of the present invention, the density for the polymer phase is assumed to be 0.95 gm/cc in all cases, even though it is recognized that each polymer has a different density. The density of the nanocomposite was estimated using a rule of mixtures, and an assumed density of the clay of 2 gm/cc.

The thickness of the coating on a substrate is measured after the OTR is reported. Each sample is removed from the Mocon module and a circle of specified size is cut from the sample. The cut circle is weighed. The weight of the coating is obtained from subtracting the weight of the uncoated circle, and the thickness calculated from the size of the circle and weight of the coating. For coating thickness less than 5 microns, the thickness is measured using an optical profilometer. The thickness of the film is reported in millimeters and used to calculate the permeability of the film.

The permeability of the coatings is calculated as follows:

$$\text{Permeability of barrier coating} = \frac{X_1}{[(1/OTR) - (X_2/P_{X2})]}$$

where $X_1$ is the barrier coating thickness; $X_2$ is substrate thickness, $P_{X2}$ is permeability of the substrate, and OTR is oxygen transmission rate measured for the barrier coating. The reduction in permeability is calculated as follows:

$$\text{Reduction in permeability} = \left[1 - \frac{\text{Permeability of a barrier coating prepared according to the inventive method}}{\text{Permeability of a barrier coating prepared by other method}}\right] \times 100\%$$

The benefit of obtaining the permeability of the coating versus the OTR of the sample is that permeability reports the OTR at a specified thickness. Therefore, coatings with different thicknesses can be compared directly. OTR units are cc/m² day at 1 atmosphere, 0% relative humidity at 23° C.

Barrier Coating Example 1A: 5% Solids Polyester Nanocomposite Using SCPX-2973 Montmorillonite Slurry In an 8 oz jar, 0.02 grams of Acusol® 880 (35.2%, Rohm & Haas), 0.05 grams of Acusol® 882 (17.1%, Rohm & Haas) and 41.54 grams of distilled water were weighed. A stir bar was added and the solution was stirred until the Acusol® materials were dissolved. To this solution was added a mixture of 5.65 grams of polyester latex (Eastek 1000, Eastman) and 1 drop of Surfynol® PSA 336 (Air Products, 100%). The resulting solution was mixed thoroughly.

To the above solution, 14.25 grams of montmorillonite SCPX-2973 slurry (9.21% silicate filler) was mixed with 3.49 grams of glycine (Lab Safety Supply, 20% glycine by weight) and 10 grams of distilled water. The resulting solution was stirred with a stir bar for 1 hour and 1 drop of Mergal® 680 (Troy Chemical Corporation, 26.3% by weight anti-microbial) was added. The percent solids of the formulation were measured as 5.0%, using standard techniques.

After this coating solution is applied to a polyester film substrate and allowed to dry, the coating contains 45.4% by weight polyester, 35.1% by weight filler, 18.7% glycine, 0.3% Surfynol® PSA 336 wetting agent, 0.2% by weight Acusol® 880, 0.2% by weight Acusol® 882 and 0.05% by weight Mergal® 680 anti-microbial agent.

The oxygen transmission rate, (OTR) is measured using a MOCON® OX-TRAN 2/20 module. The OTR is 11.9 cc/m² day@ 1 atmosphere, 0% RH, 23° C. Permeability of the 0.5 micron polyester nanocomposite is 0.008 cc mm/m² day atmosphere@ 0% RH, 23° C. The reduction in permeability of this coating is 337 times the reduction in permeability of a coating made from the unfilled polyester latex.

Barrier Coating Example 1B: 8% Solids Polyester Nanocomposite Using SCPX-2973 Montmorillonite Slurry In an 8 oz jar, 0.04 grams of Acusol® 880 (35.2%, Rohm & Haas), 0.08 grams of Acusol®D 882 (17.1%, Rohm & Haas) and 37.4 grams of distilled water were weighed. A stir bar was added and the solution was stirred until the Acusol® materials were dissolved. To this solution was added a mixture of 9.0 grams of polyester latex (Eastek 1000, Eastman) and 1 drop of Surfynol® PSA 336 (Air Products, 100%). The resulting solution was mixed thoroughly.

To the above solution, 22.8 grams of montmorrillonite SCPX-2973 slurry (9.21%) was mixed with 5.59 grams of glycine (Lab Safety Supply, 20%). The resulting solution was stirred with a stir bar for 1 hour and 1 drop of Mergal® 680 (Troy Chemical Corporation, 26.3%) was added. The percent solids of the formulation were measured as 8.1% using standard techniques.

After this coating solution is applied to a polyester film substrate and allowed to dry, the coating contains 45.4% by weight polyester, 35.1% by weight filler, 18.7% glycine, 0.3% Surfynol® PSA 336 wetting agent, 0.2% by weight Acusol® 880, 0.2% by weight Acusol® 882 and 0.05% by weight Mergal® 680 anti-microbial agent.

The oxygen transmission rate (OTR) is measured using a MOCON® OX-TRAN 2/20 module. The OTR is 6.1 cc/m$^2$ day@ 1 atmosphere, 0% RH, 23° C. Permeability of the 0.6 micron polyester nanocomposite is 0.004 cc mm/m$^2$ day atmosphere@ 0% RH, 23° C. The reduction in permeability of this coating is 675 times the reduction in permeability of a coating made from the unfilled polyester latex.

Barrier Coating Example 1C: 8% Solids Polyester Nanocomposite Using SCPX-2973 Montmorillonite Slurry Concentrated from Example 1A 50 grams of the nanocomposite from example 1A was placed in an 8 oz. jar. The jar with the lid removed was then placed into a water bath at 95° C. for 90 min while stirring. The internal temperature of the formulation was maintained at 75° C. After the allotted time, the formulation was removed from the water bath and stirred overnight with the lid replaced. The percent solids of the concentrated formulation were measured as 8.3% using standard techniques.

After this coating solution is applied to a polyester film substrate and allowed to dry, the coating contains 45.4% by weight polyester, 35.1% by weight filler, 18.7% glycine, 0.3% Surfynol® PSA 336 wetting agent, 0.2% by weight Acusol® 880, 0.2% by weight Acusol® 882 and 0.05% by weight Mergal® 680 anti-microbial agent.

The oxygen transmission rate (OTR) is measured using a MOCON® OX-TRAN 2/20 module. The OTR is 5.0 cc/m$^2$ day@1 atmosphere, 0% RH, 23° C. Permeability of the 0.6 micron polyester nanocomposite is 0.003 cc mm/m$^2$ day atmosphere@ 0% RH, 23° C. The reduction in permeability of this coating is 900 times the reduction in permeability of a coating made from the unfilled polyester latex. The permeability is also 25% lower than the dispersion that was prepared at a target solids content of 8%.

Barrier Coating Example 2A: 5% Solids Polyester Nanocomposite Using SCPX-2953 Montmorillonite Solid In a 16 oz jar, 0.05 grams of Acusol® 880 (35.2%, Rohm & Haas), 0.1 grams of Acusol® 882 (17.1%, Rohm & Haas) and 78.9 grams of distilled water were weighed. A stir bar was added and the solution was stirred until the Acusol materials were dissolved. To this solution was added a mixture of 11.3 grams of polyester latex (Eastek 1000, Eastman) and 2 drop of Surfynol® PSA 336 (Air Products, 100%). The resulting solution was mixed thoroughly.

To the above solution, 2.63 grams of montmorillonite SCPX-2953 solid (100%) was mixed with 6.98 grams of glycine (Lab Safety Supply, 20%) and 50 grams of distilled water. The resulting solution was stirred with a stir bar for 1 hour and 2 drops of Mergal® 680 (Troy Chemical Corporation, 26.3%) was added. The percent solids of the formulation were measured as 4.8% using standard techniques.

After this coating solution is applied to a polyester film substrate and allowed to dry, the coating contains 45.4% by weight polyester, 35.1% by weight filler, 18.7% glycine, 0.3% Surfynol® PSA 336 wetting agent, 0.2% by weight Acusol® 880, 0.2% by weight Acusol® 882 and 0.05% by weight Mergal® 680 anti-microbial agent.

The oxygen transmission rate (OTR) is measured using a MOCON® OX-TRAN 2/20 module. The OTR is 6.5 cc/m$^2$ day@ 1 atmosphere, 0% RH, 23° C. Permeability of the 0.5 micron polyester nanocomposite is 0.004 cc mm/m$^2$ day atmosphere@ 0% RH, 23° C. The reduction in permeability of this coating is 675 times the reduction in permeability of a coating made from the unfilled polyester latex.

Barrier Coating Example 2B: 8% Solids Polyester Nanocomposite Using SCPX-2953 Montmorillonite Solid In an 8 oz jar, 0.04 grams of Acusol® 880 (35.2%, Rohm & Haas), 0.09 grams of Acusol® 882 (17.1%, Rohm & Haas) and 38.16 grams of distilled water were weighed. A stir bar was added and the solution was stirred until the Acusol materials were dissolved. To this solution was added a mixture of 9.0 grams of polyester latex (Eastek 1000, Eastman) and 1 drop of Surfynol® PSA 336 (Air Products, 100%). The resulting solution was mixed thoroughly.

To the above solution, 2.1 grams of montmorrillonite SCPX-2953 solid (100%) was mixed with 5.59 grams of glycine (Lab Safety Supply, 20%) and 20 grams of distilled water. The resulting solution was stirred with a stir bar for 1 hour and 1 drop of Mergal® 680 (Troy Chemical Corporation, 26.3%) was added. The percent solids of the formulation were measured as 7.8% using standard techniques.

After this coating solution is applied to a polyester film substrate and allowed to dry, the coating contains 45.4% by weight polyester, 35.1% by weight filler, 18.7% glycine, 0.3% Surfynol® PSA 336 wetting agent, 0.2% by weight Acusol® 880, 0.2% by weight Acusol® 882 and 0.05% by weight Mergal® 680 anti-microbial agent.

The oxygen transmission rate (OTR) is measured using a MOCON® OX-TRAN 2/20 module. The OTR is 11.5 cc/m$^2$ day@1 atmosphere, 0% RH, 23° C. Permeability of the 0.6 micron polyester nanocomposite is 0.009 cc mm/m$^2$ day atmosphere@ 0% RH, 23° C. The reduction in permeability of this coating is 300 times the reduction in permeability of a coating made from the unfilled polyester latex.

Barrier Coating Example 2C: 8% Solids Polyester Nanocomposite Using SCPX-2953 Montmorillonite Solid Concentrated from Example 2A 50 grams of the nanocomposite formulation of example 2A was placed in an 8 oz. jar. The jar with the lid removed was then placed into a water bath at 95° C. for 90 min while stirring. The internal temperature of the formulation was maintained at 75° C. After the allotted time, the formulation was removed from the water bath and stirred overnight with the lid replaced. The percent solids of the formulation was measured as 7.8% using standard techniques.

After this coating solution is applied to a polyester film substrate and allowed to dry, the coating contains 45.4% by weight polyester, 35.1% by weight filler, 18.7% glycine, 0.3% Surfynol® PSA 336 wetting agent, 0.2% by weight Acusol® 880, 0.2% by weight Acusol® 882 and 0.05% by weight Mergal® 680 anti-microbial agent.

The oxygen transmission rate (OTR) is measured using a MOCON® OX-TRAN 2/20 module. The OTR is 3.0 cc/m² day@1 atmosphere, 0% RH, 23° C. Permeability of the 0.6 micron polyester nanocomposite is 0.002 cc mm/m² day atmosphere@ 0% RH, 23° C. The reduction in permeability of this coating is 1350 times the reduction in permeability of a coating made from the unfilled polyester latex. The permeability is also 78% lower than the dispersion that was prepared at a target solids content of 8%.

Barrier Coating Example 3A: 5% Solids Polyester Nanocomposite Using SCPX-2041 Montmorillonite Solid In a 16 oz jar, 0.05 grams of Acusol® 880 (35.2%, Rohm & Haas), 0.1 grams of Acusol® 882 (17.1%, Rohm & Haas) and 78.94 grams of distilled water were weighed. A stir bar was added and the solution was stirred until the Acusol® materials were dissolved. To this solution was added a mixture of 11.3 grams of polyester latex (Eastek 1000, Eastman) and 2 drop of Surfynol® PSA 336 (Air Products, 100%). The resulting solution was mixed thoroughly.

To the above solution, 2.63 grams of montmorillonite SCPX-2041 solid (100%) was mixed with 6.98 grams of glycine (Lab Safety Supply, 20%) and 50 grams of distilled water. The resulting solution was stirred with a stir bar for 1 hour and 2 drops of Mergal® 680 (Troy Chemical Corporation, 26.3%) was added. The percent solids of the formulation were measured as 5.0% using standard techniques.

After this coating solution is applied to a polyester film substrate and allowed to dry, the coating contains 45.4% by weight polyester, 35.1% by weight filler, 18.7% glycine, 0.3% Surfynol® PSA 336 wetting agent, 0.2% by weight Acusol® 880, 0.2% by weight Acusol® 882 and 0.05% by weight Mergal® 680 anti-microbial agent.

The oxygen transmission rate (OTR) is measured using a MOCON® OX-TRAN 2/20 module. The OTR is 17.1 cc/m² day@ 1 atmosphere, 0% RH, 23° C. Permeability of the 0.5 micron polyester nanocomposite is 0.013 cc mm/m² day atmosphere@ 0% RH, 23° C. The reduction in permeability of this coating is 207 times the reduction in permeability of a coating made from the unfilled polyester latex.

Barrier Coating Example 3B: 8% Solids Polyester Nanocomposite Using SCPX-2041 Montmorillonite Solid In an 8 oz jar, 0.04 grams of Acusol® 880 (35.2%, Rohm & Haas), 0.09 grams of Acusol® 882 (17.1%, Rohm & Haas) and 38.16 grams of distilled water were weighed. A stir bar was added and the solution was stirred until the Acusol® materials were dissolved. To this solution was added a mixture of 9.02 grams of polyester latex (Eastek 1000, Eastman) and 1 drop of Surfynol® PSA 336 (Air Products, 100%). The resulting solution was mixed thoroughly.

To the above solution, 2.1 grams of montmorillonite SCPX-2041 solid (100%) was mixed with 5.59 grams of glycine (Lab Safety Supply, 20%) and 20 grams of distilled water. The resulting solution was stirred with a stir bar for 1 hour and 1 drop of Mergal® 680 (Troy Chemical Corporation, 26.3%) was added. The percent solids of the formulation were measured as 7.8% using standard techniques.

After this coating solution is applied to a polyester film substrate and allowed to dry, the coating contains 45.4% by weight polyester, 35.1% by weight filler, 18.7% glycine, 0.3% Surfynol® PSA 336 wetting agent, 0.2% by weight Acusol® 880, 0.2% by weight Acusol® 882 and 0.05% by weight Mergal® 680 anti-microbial agent.

The oxygen transmission rate (OTR) is measured using a MOCON® OX-TRAN 2/20 module. The OTR is 9.7 cc/m² day@ 1 atmosphere, 0% RH, 23° C. Permeability of the 0.6 micron polyester nanocomposite is 0.007 cc mm/m² day atmosphere@ 0% RH, 23° C. The reduction in permeability of this coating is 386 times the reduction in permeability of a coating made from the unfilled polyester latex.

Barrier Coating Example 3C: 8% Solids Polyester Nanocomposite Using SCPX-2041 Montmorillonite Solid Concentrated from Example 3A 50 grams of the nanocomposite formulation from Example 3A was placed in an 8 oz. jar. The jar with the lid removed was then placed into a water bath at 95° C. for 90 min while stirring. The internal temperature of the formulation was maintained at 75° C. After the allotted time, the formulation was removed from the water bath and stirred overnight with the lid replaced. The percent solids of the formulation were measured as 9.0% using standard techniques.

After this coating solution is applied to a polyester film substrate and allowed to dry, the coating contains 45.4% by weight polyester, 35.1% by weight filler, 18.7% glycine, 0.3% Surfynol® PSA 336 wetting agent, 0.2% by weight Acusol® 880, 0.2% by weight Acusol® 882 and 0.05% by weight Mergal® 680 anti-microbial agent.

The oxygen transmission rate (OTR) is measured using a MOCON® OX-TRAN 2/20 module. The OTR is 7.5 cc/m² day@ 1 atmosphere, 0% RH, 23° C. Permeability of the 0.6 micron polyester nanocomposite is 0.005 cc mm/m² day atmosphere@ 0% RH, 23° C. The reduction in permeability of this coating is 540 times the reduction in permeability of a coating made from the unfilled polyester latex. The permeability is also 28% lower than the dispersion that was prepared at a target solids content of 8%.

The permeability data for Examples 1A through 3C are outlined in 6, below.

TABLE 6

Summary of Results

| Example | Oxygen Permeability (cc mm/m2 day atm @ 23 C., 0% RH) | | |
|---|---|---|---|
| | 5% solid | 8% as made | 8% concentrated |
| Ex. 1A-1C SCPX-2973 slurry | 0.008 | 0.004 | 0.003 |
| Ex. 2A-2C SCPX-2953 solid | 0.0035 | 0.009 | 0.0025 |
| Ex. 3A-3C SCPX-2041 solid | 0.013 | 0.007 | 0.005 |

Figure 8:
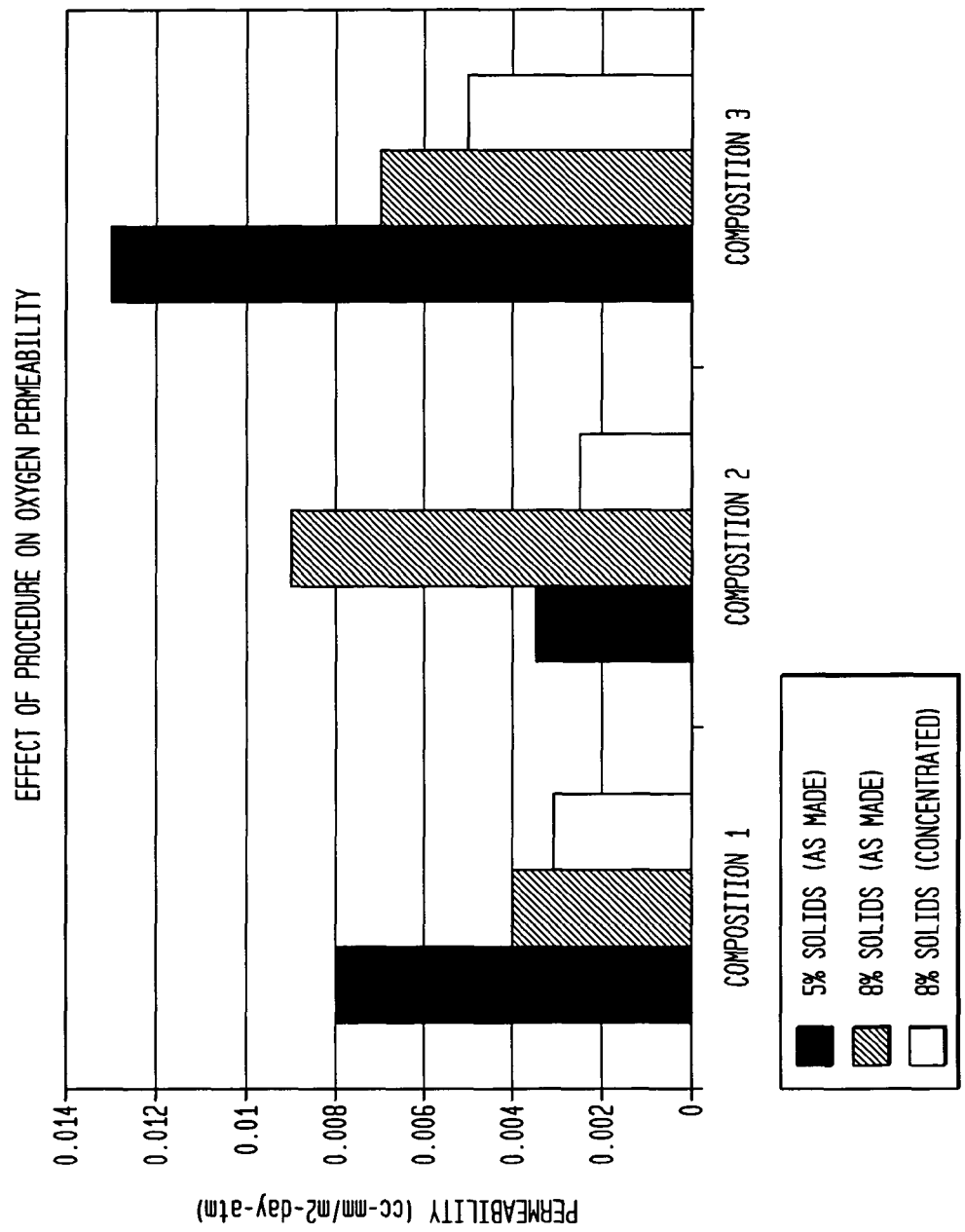
FIG. 8 is a diagram showing the oxygen permeability values of three compositions prepared according to different methods, where it is seen that the concentrated dispersions have the lowest permeability.

The above results are further illustrated in FIG. 8, where it can be seen that for each composition, the 8% concentrated dispersions of the invention achieved the best barrier properties. This is surprising because, aside from the method of preparation, one would think that the composition and structure would be substantially identical to those which were prepared at an 8% solids level. Moreover, the improvement is dramatic, with the concentrated dispersions providing coatings which have permeability values which are 20% lower than the 8% as-made composition, and in some instances show improvements of more than 70%.

While the foregoing Examples describe some preferred nanocomposites for use in connection with the present invention, the following copending patent applications and issued patents, the disclosures of which are incorporated herein by reference, provide further details and examples of suitable composites which may be used as a barrier coating: U.S. patent application Ser. No. 11/901,192, filed Sep. 14, 2007, entitled "Concentrated Aqueous Nanocomposite Dispersions for Barrier Coatings"; U.S. patent application Ser. No. 11/272,351 (United States Patent Application Publication No. US 2006-0110615), filed Nov. 10, 2005, entitled "Multilayer Nanocomposite Barrier Structures"; U.S. patent application Ser. No. 11/113,349 (United States Patent Application Publication No. US 2005-0228104), filed Apr. 22, 2005, entitled "Barrier Coating Mixtures Containing Non-Elastomeric Acrylic Polymer With Silicate Filler and Coated Articles", now U.S. Pat. No. 7,473,739 issued Jan. 6, 2009; U.S. patent application Ser. No. 10/741,741 (United States Patent Application Publication No. US 2007-0213446 A1), filed Dec. 19, 2003, entitled "Barrier Coating of a Non-Elastomeric Polymer and a Dispersed Layered Filler in a Liquid Carrier and Coated Articles"; U.S. Pat. No. 7,119,138, issued Oct. 10, 2006, entitled "Barrier Coating of a Mixture of Cured and Uncured Elastomeric Polymers and a Dispersed Layered Filler in a Liquid Carrier and Coated Articles", to Feeney et al.; and U.S. Pat. No. 7,078,453, issued Jul. 18, 2006, entitled "Barrier Coating of a Non-Butyl Elastomer and a Dispersed Layered Filler in a Liquid Carrier and Coated Articles", to Feeney et al.

It has also been found that invisible marker dyes, that is, those which exhibit strong absorbency outside of the visible spectrum (i.e., at wavelengths less than 400 nm or greater than 700 nm) can be used to measure thickness of certain nanocomposite barrier coatings without adversely impacting optical properties of the products with respect to visible light. To this end, nanocomposite coating compositions were prepared as described above, except that an invisible marker dye was added to the aqueous dispersion prior to applying the coating composition to a substrate. Details appear below.

Barrier Coating Example 4: Thickness Correlation Using Near Infrared (NIR) Dye

Two dyes, SDA 8700 and SDB 4927, were purchased from H.W. Sands Corp., and were screened as markers for thickness measurement. Specimens similar to those of Example 3C containing the SDB 4927 dye (35 percent filler material with 8 percent total solids and containing 20 mg/L dye concentration) for different dipping times to get a range of thicknesses. Absorbance spectra were measured at different points on glass slides in an Evolution 300 spectrometer. Thicknesses on glass slides were measured using Optical Profilometry. Absorbance spectra and film thickness were measured at the same region of the glass slides. The two measurements average over different size and shaped areas. The absorbance peak area calculated using a polynomial fit to the background base line showed the best correlation with thickness with a linear trend (with regression, $R^2=0.93$) compared to peak height and peak areas using a linear baseline. The dye is also stable in formulation for minimum of eight weeks as further described in detail below.

Barrier Coating Example 4A: Preparation of Aqueous Dye Solution

Figure 9:
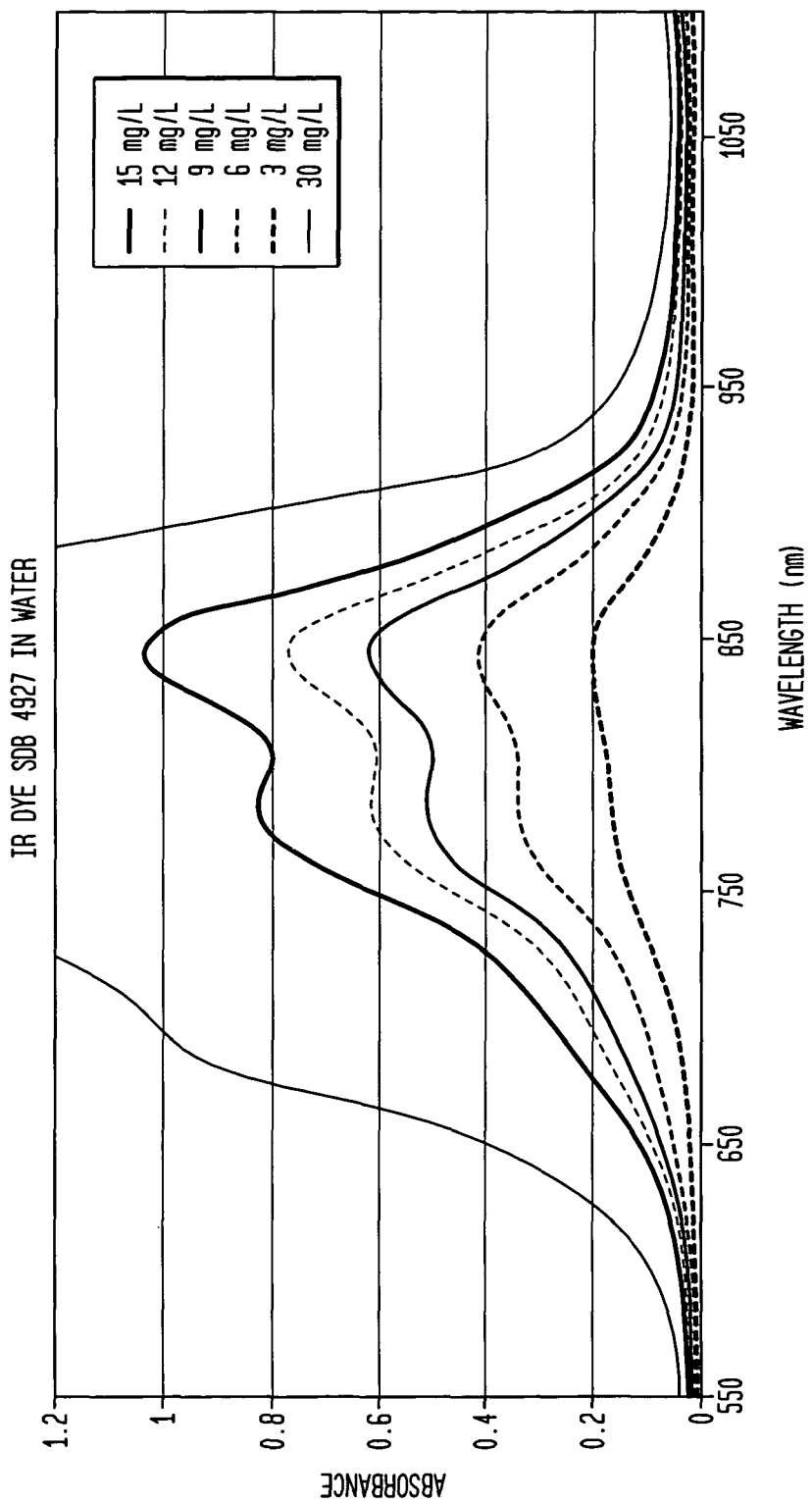
FIG. 9 is an absorbance spectrum of different concentrations of SDB 4927 invisible marker dye in water.
Figure 10:
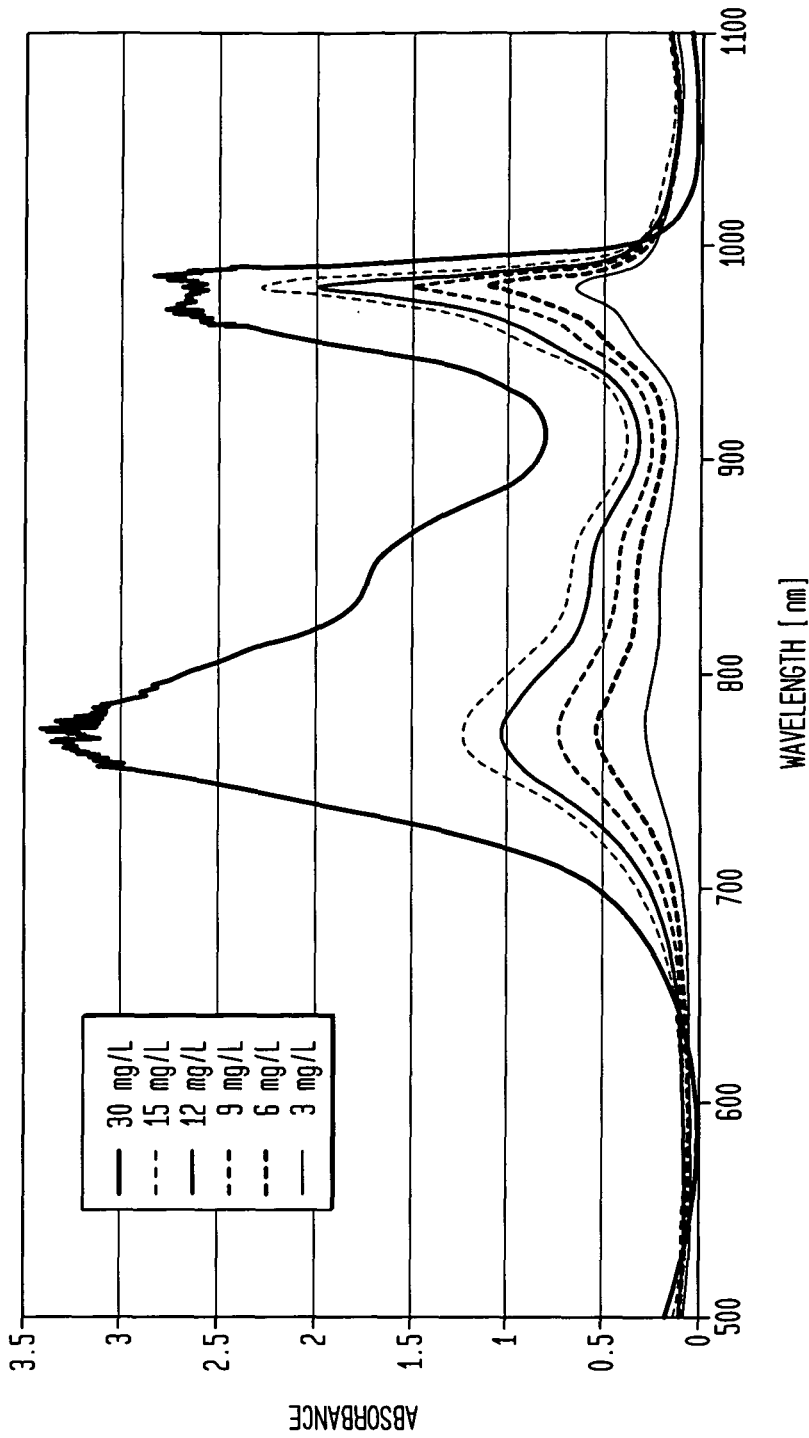
FIG. 10 is an absorbance spectrum of different concentrations of SDA 8700 invisible marker dye in water.
Figure 11:
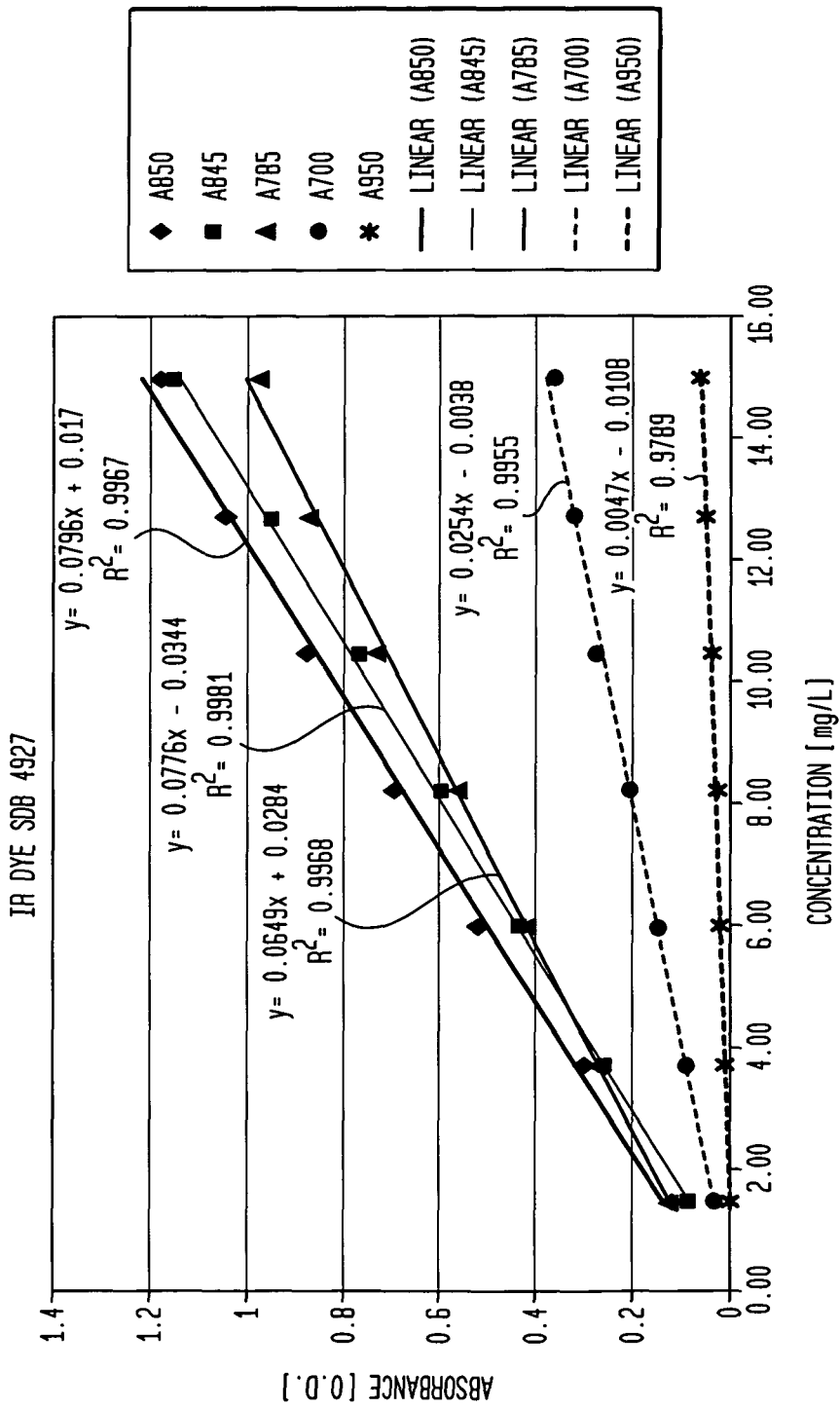
FIG. 11 is an absorbance at different wavelength for various concentrations of SDB 4927 invisible marker dye in water, which shows a linear trend within the measured concentration range.

The dye samples were dissolved in water to form a master batch containing a dye concentration of 10 mg/100 mL and diluted as needed to obtain a series of aqueous SDB 4927 and SDA 8700 solution samples. The absorbance spectra of these solutions were measured from 500 to 1100 nm. FIG. 9 and FIG. 10 respectively show the absorbance spectra of different concentrations of SDB 4927 and SDA 8700. As it is apparent from these figures for all of the concentration range studied, the nature of the peak remained same. The highest intensity peak was observed at 846 nm for SDB 4927. Absorption followed linear trend with dye concentration with regression, $R^2=0.99$ as shown in FIG. 11. A broader absorbance peak was observed for SDA 8700 dye. Comparatively narrow absorbance peak was observed for SDB 4927 dye in the near infrared region.

Barrier Coating Example 4B: Preparation of Dye Containing Barrier Coating Compositions Compositions similar to Example 3C were used in this Example 4B. A measured amount of SDB 4927 dye (NIR dye powder) was added to the nanocomposite formulation in a plastic bottle and stirred using magnetic stirrer for approximately 16 hrs. Two samples of coating compositions containing SDB 4927 dye at concentrations of 10 mg/100 mL and 10 mg/L were prepared. Similarly, two additional samples of coating compositions containing SDA 8700 at concentrations of 10 mg/100 mL and 10 mg/L were also prepared.

Films were prepared of all four formulations on 1 mil PET film and the oxygen transmission rate (OTR) was tested. The intent was to determine if there was any effect of the dye on the barrier property of the formulation. OTR of films with the starting formulation was also run. All barrier coatings can be considered as the same thickness within experimental error. The results are tabulated in Table 7. The results clearly demonstrate that the dye does not affect the oxygen transmission rate.

TABLE 7

Summary of Results

| Formulation | Dye | Concentration mg/L | OTR cc/m2 day atm @ 23 C., 0% RH | |
| --- | --- | --- | --- | --- |
| Control | none | 0 | 1.9 | 1.0 |
| 1 | SDB4927 | 10 | 1.5 | 0.9 |
| 2 | SDB4927 | 100 | 1.5 | 1.5 |
| 3 | SDA8700 | 10 | 2.0 | 1.4 |
| 4 | SDA8700 | 100 | 1.8 | 1.3 |

Figure 12:
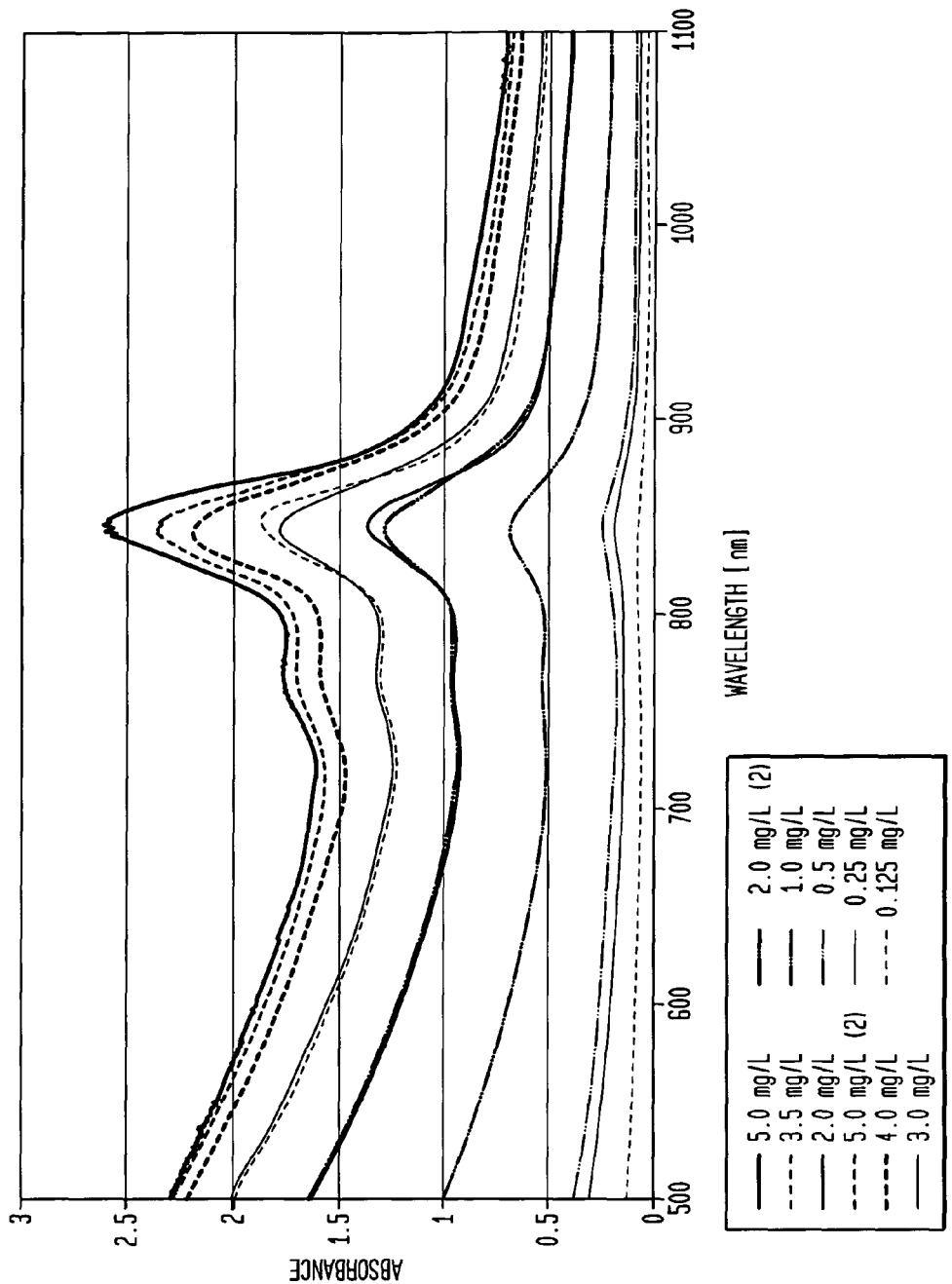
FIG. 12 is an absorbance spectra of SDB 4927 dye containing barrier coating composition of Example 4 (8 weight percent total solids with 10 mg/L of SDB 4927 dye resulting in 35 weight percent of montmorillonite in the dried coating) diluted in water to various concentration.

The SDB 4927 dye containing formulations were then diluted to various concentrations and absorption spectra were taken and is shown in FIG. 12. It is evident from this Figure that the nature of the peak remained same as in FIG. 9 and the peak did not shift.

Figure 13:
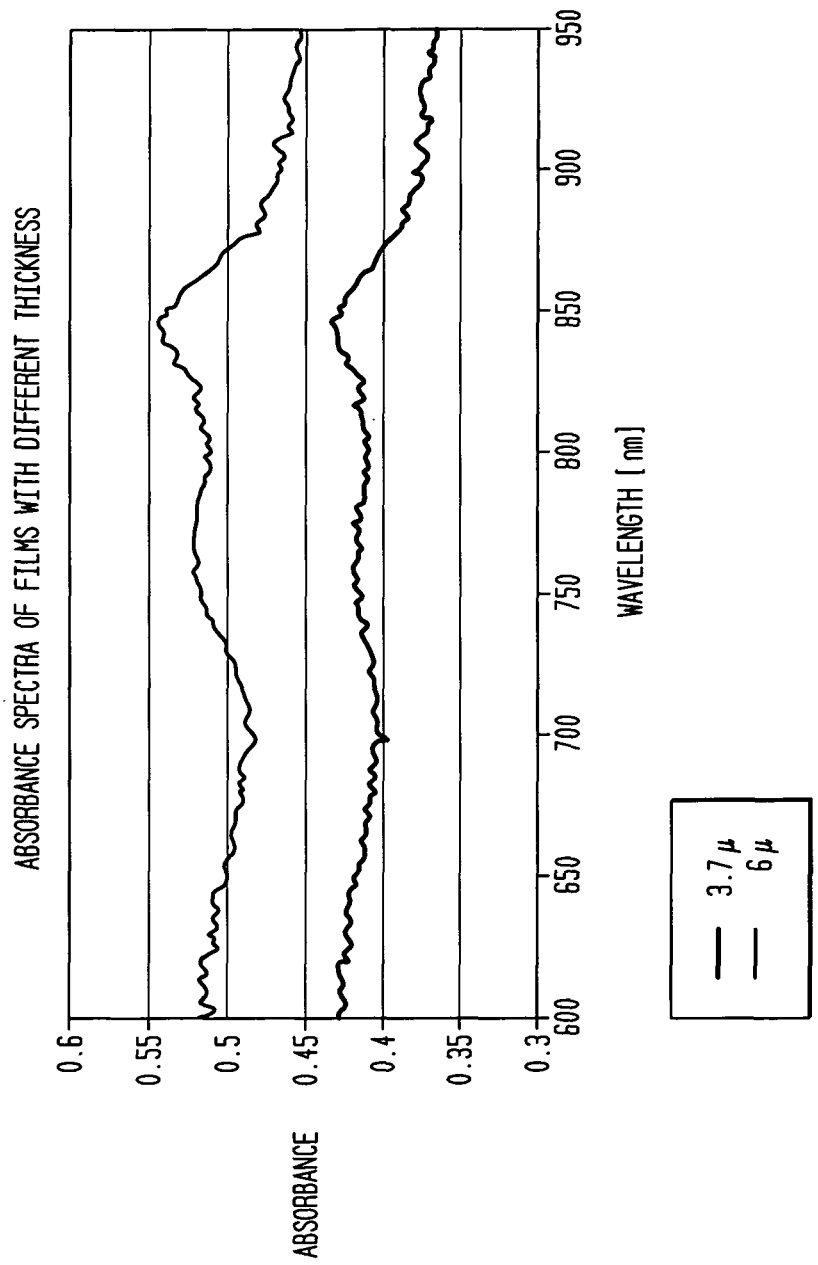
FIG. 13 is an absorbance spectra of coated BOPP substrates, which are coated with SDB 4927 dye containing barrier composition of Example 4 (8 weight percent total solids with 20 mg/L of SDB 4927 dye resulting in 35 weight percent of montmorillonite in the dried coating)
Figure 14:
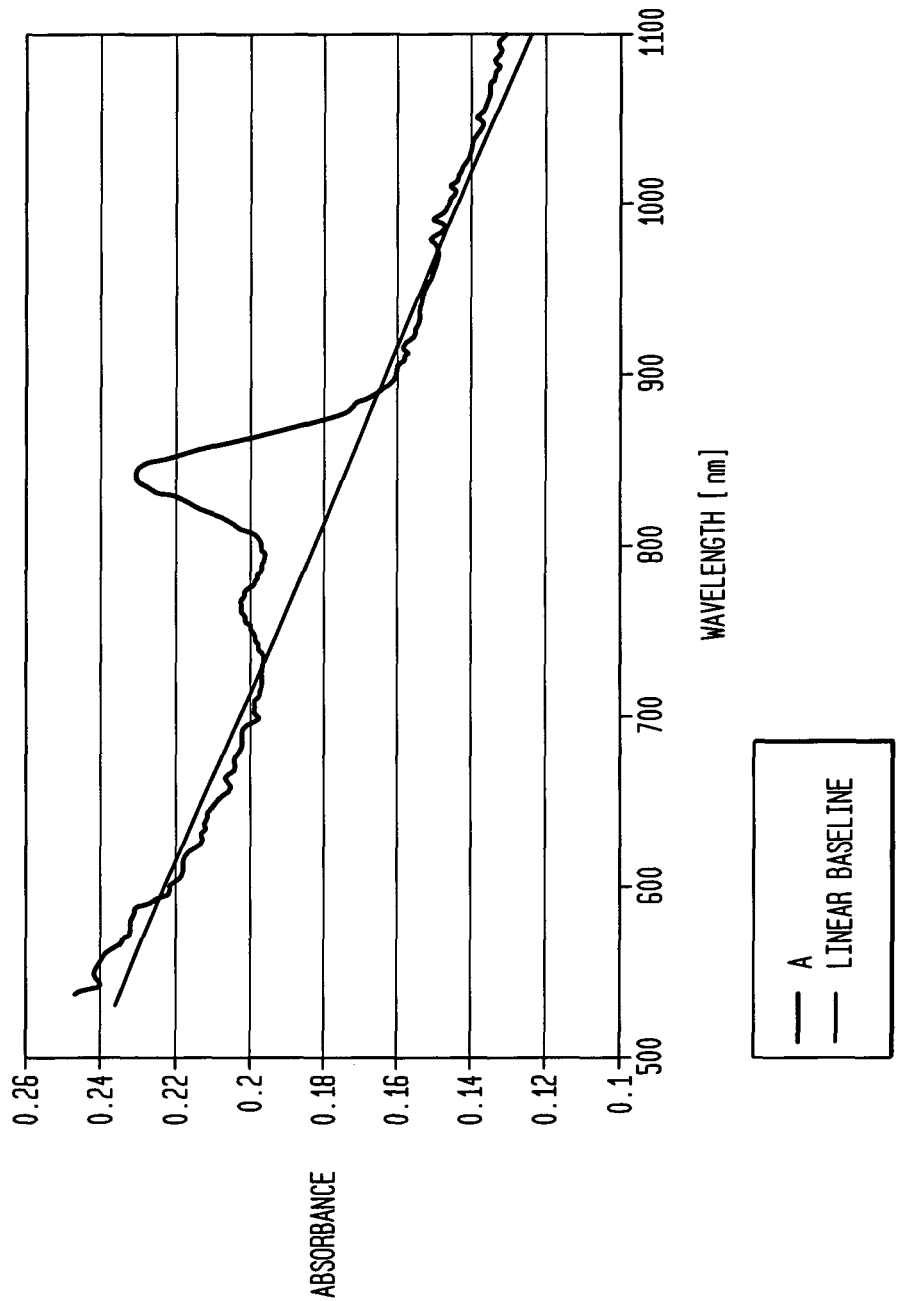
FIG. 14 is an absorbance spectrum of film with a linear baseline, the film was formed from SDB 4927 dye containing barrier composition of Example 5 (8 weight percent total solids with 20 mg/L of SDB 4927 dye resulting in 35 weight percent of montmorillonite in the dried film)

Two different thicknesses of coating (compositions containing SDB 4927 dye at concentrations of 20 mg/L) were casted on BOPP film. Thickness of the films was measured by profilometry method. The absorption spectrum was measured on coated BOPP films as shown in FIG. 13. It is evident from this figure that the nature of the peak remained same for both the film thickness.

Barrier Coating Example 5: SDB 4927 Dye Containing Coating Compositions of Example 3C to Correlate Absorbance Spectra with Linear and Polynomial Baseline This Example illustrates how to develop a coating thickness calibration curve in the 2-8 micron thickness range for freshly prepared 5 and 20 mg/L SDB 4927 dye contained in a barrier coating composition similar to Example 3C.

Figure 15:
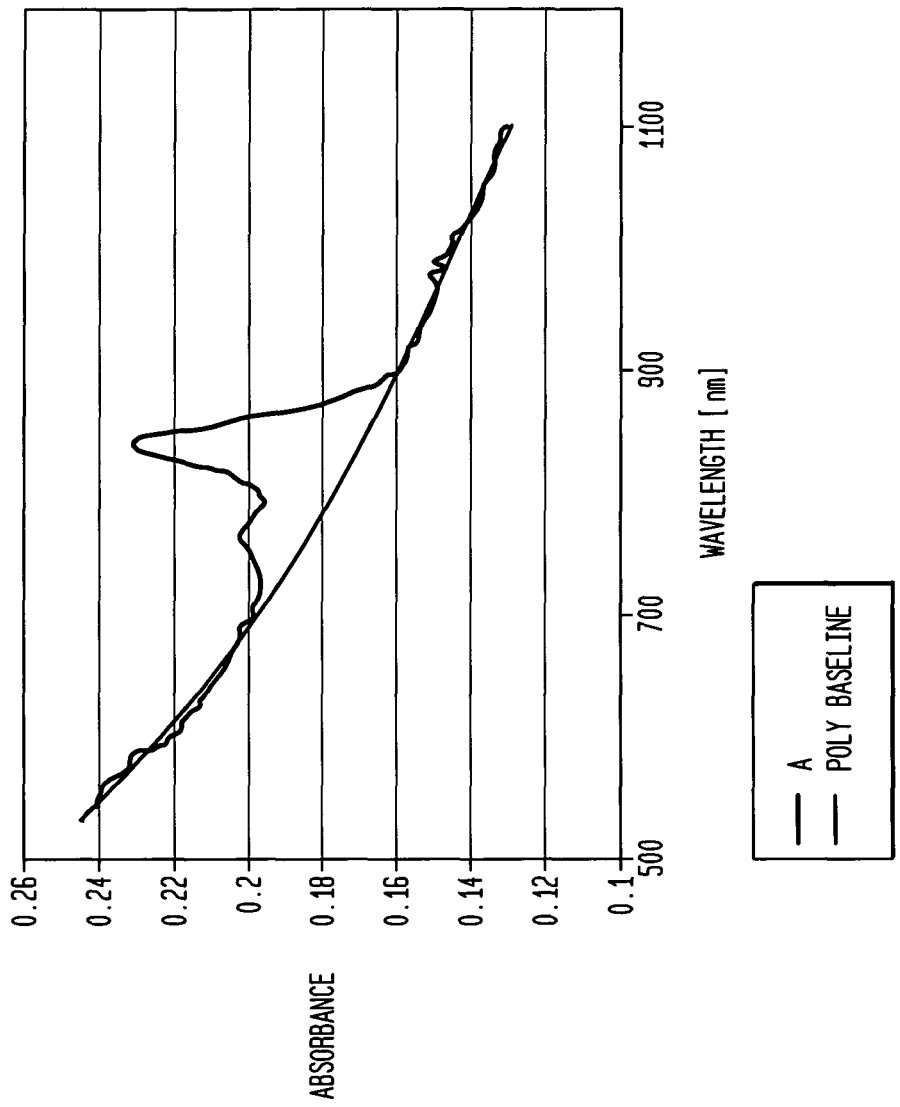
FIG. 15 is an absorbance spectrum of film with a polynomial baseline, the film was formed from SDB 4927 dye containing barrier composition of Example 5 (8 weight percent total solids with 20 mg/L of SDB 4927 dye resulting in 35 weight percent of montmorillonite in the dried film)
Figure 16:
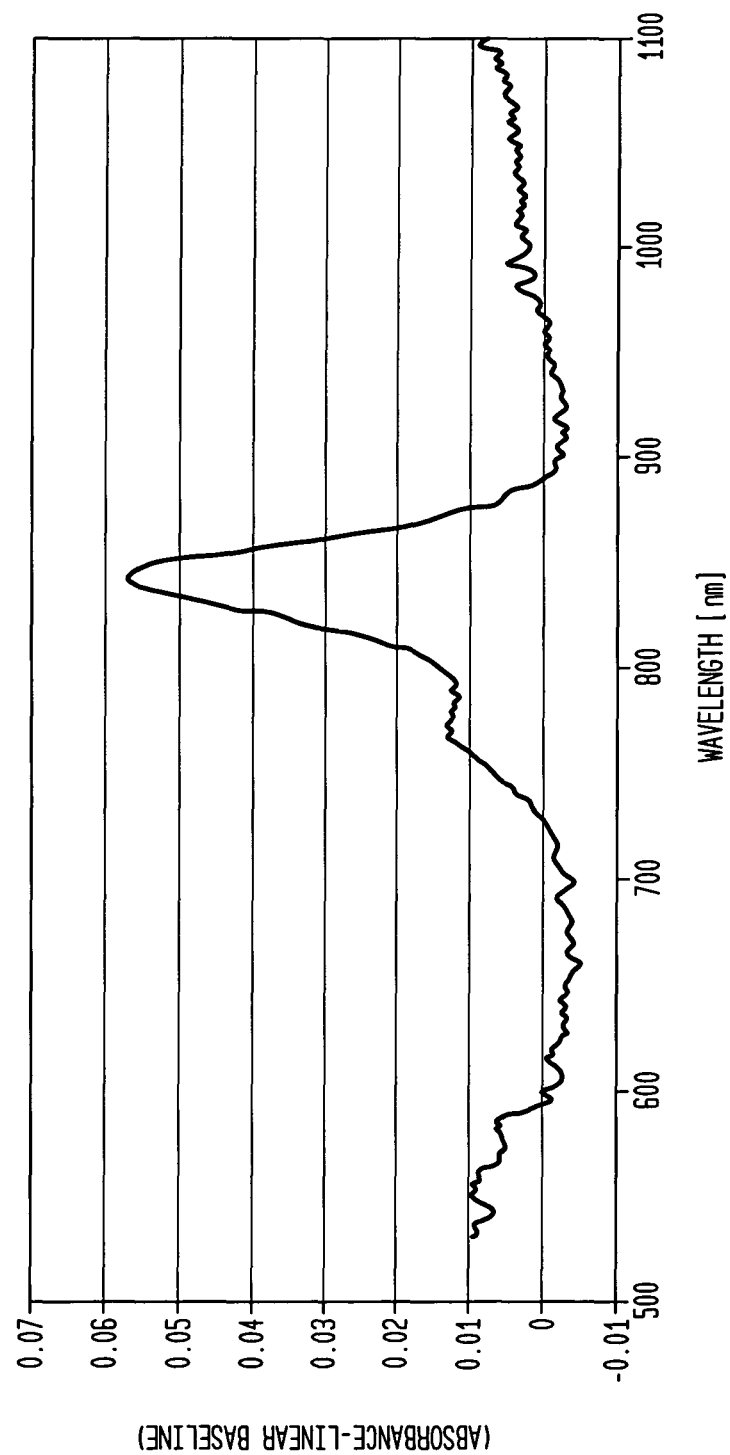
FIG. 16 is a corrected spectrum of FIG. 14 showing linear baseline subtracted absorption spectrum of film ((absorbance−linear baseline) vs. wavelength (nm))
Figure 17:
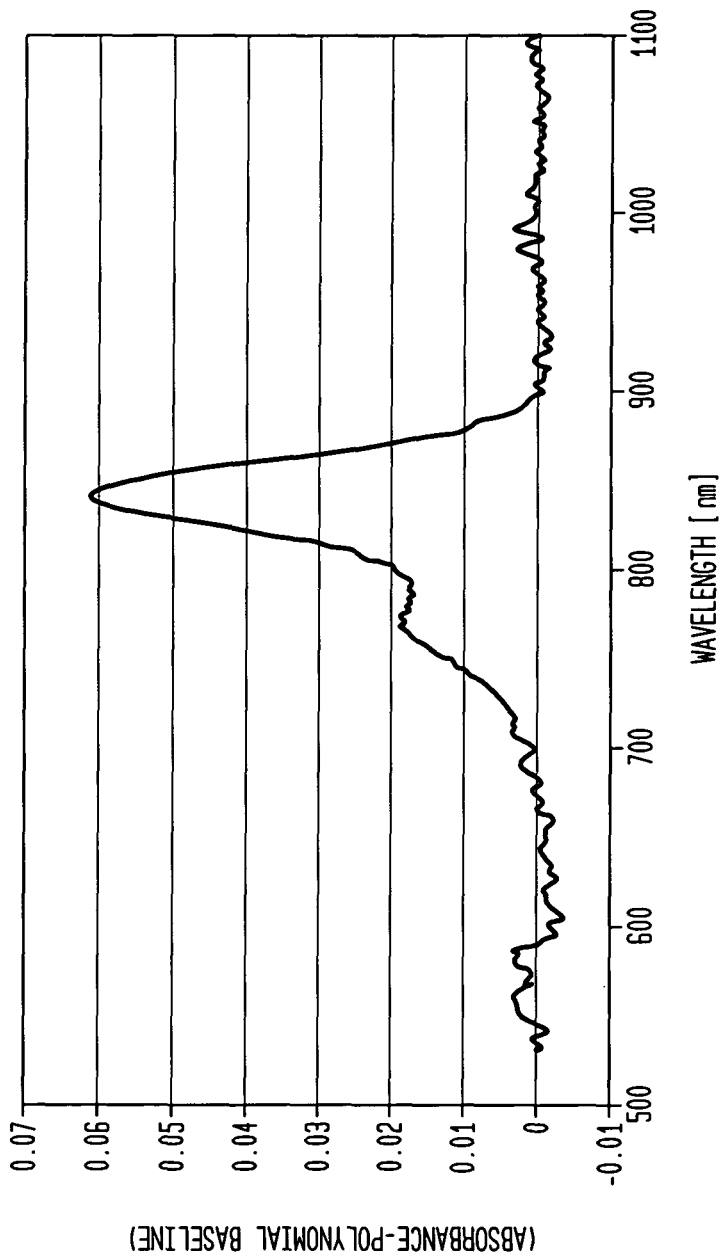
FIG. 17 is a corrected spectrum of FIG. 15 showing polynomial baseline subtracted absorption spectrum of film ((absorbance−polynomial baseline) vs. wavelength (nm))
Figure 18:
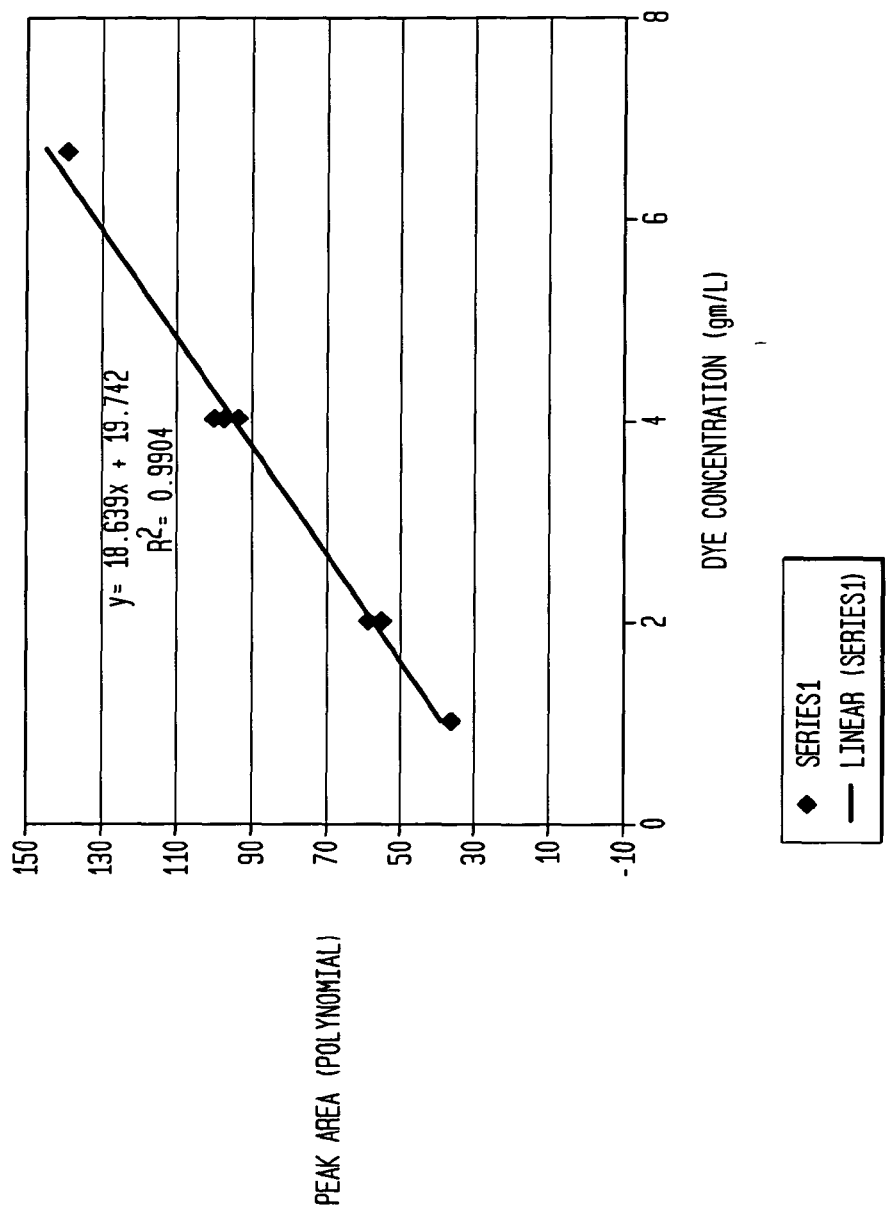
FIG. 18 illustrates a relationship with concentration of SDB 4927 dye in barrier coating composition of Example 5 and the absorbance peak area (i.e., area under the curve (AUC) at 846 nm) using polynomial baseline.

The SDB 4927 dye at a concentration of 20 mg/L in the composition of Example 3C was diluted using de-ionized (DI) water to a variety of concentrations. Absorbance specta were measured for all the concentrations. Peak height and area were determined considering linear and polynomial baseline as shown in FIGS. 14-17 and correlated with dye concentration in formulation. Linear baseline is plotted between the onset and end of the peak. The onset and end of the peak are approximately 720 and 900 nm, respectively. Linear baseline is extrapolated to 500 nm at one end and 1100 nm on the other end. Once linear base line is determined, it is subtracted from absorbance as shown in FIG. 16. For polynomial baseline, the absorbance peak data were deleted (absorbance data from ~720 to ~900 nm) and the remaining data was fitted with third order polynomial. Once polynomial baseline is determined, it is subtracted from absorbance as shown in FIG. 15 and area under the peak was determined. FIG. 18 shows the linearity of dye concentration in formulation with absorbance peak area considering the polynomial baseline. It confirms uniform solubility and distribution of dye in formulation.

Figure 19:
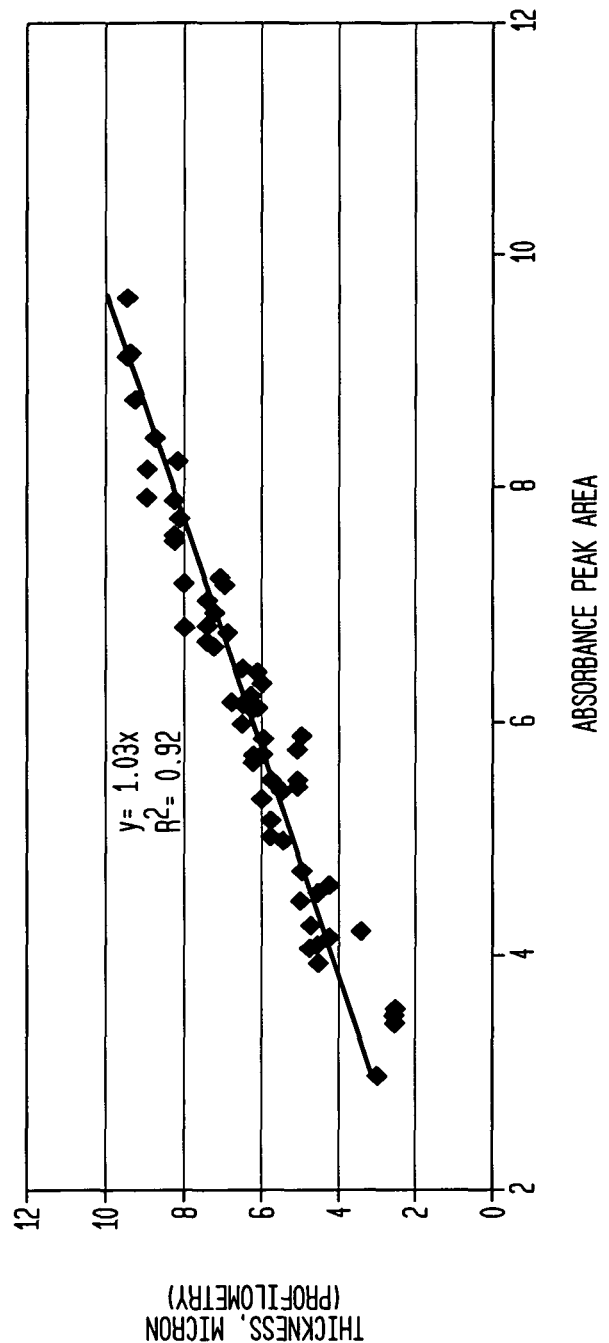
FIG. 19 shows a correlation with thickness and absorbance peak area of coatings on glass slide of Example 6, which used coating compositions as described in Example 5 (concentrated polyester-montmorillonite coating composition with 8 percent total solids containing 20 mg/L SDB 4927 dye, which resulted in 35 weight percent montmorillonite in the dried film)

Barrier Coating Example 6: SDB 4927 Dye Containing Coating Compositions to Correlate Absorbance Spectra and Thickness on Coated Glass Slides Glass slides were coated with SDB 4927 dye at 20 mg/L concentration in the formulation otherwise similar to Example 3C for different dipping times to get a range of thicknesses. Absorbance spectra were measured at different points on the glass slide. Thicknesses were measured using Optical Profilometry. Absorbance spectra and film thickness were measured at the same point within experimental error. The peak area considering polynomial base line showed better correlation with thickness. The peak area was correlated with thickness measured by Profilometry as shown in FIG. 19. As shown in FIG. 19, the peak area of the SDB 4927 dye is linear with thickness of coating.

Figure 20:
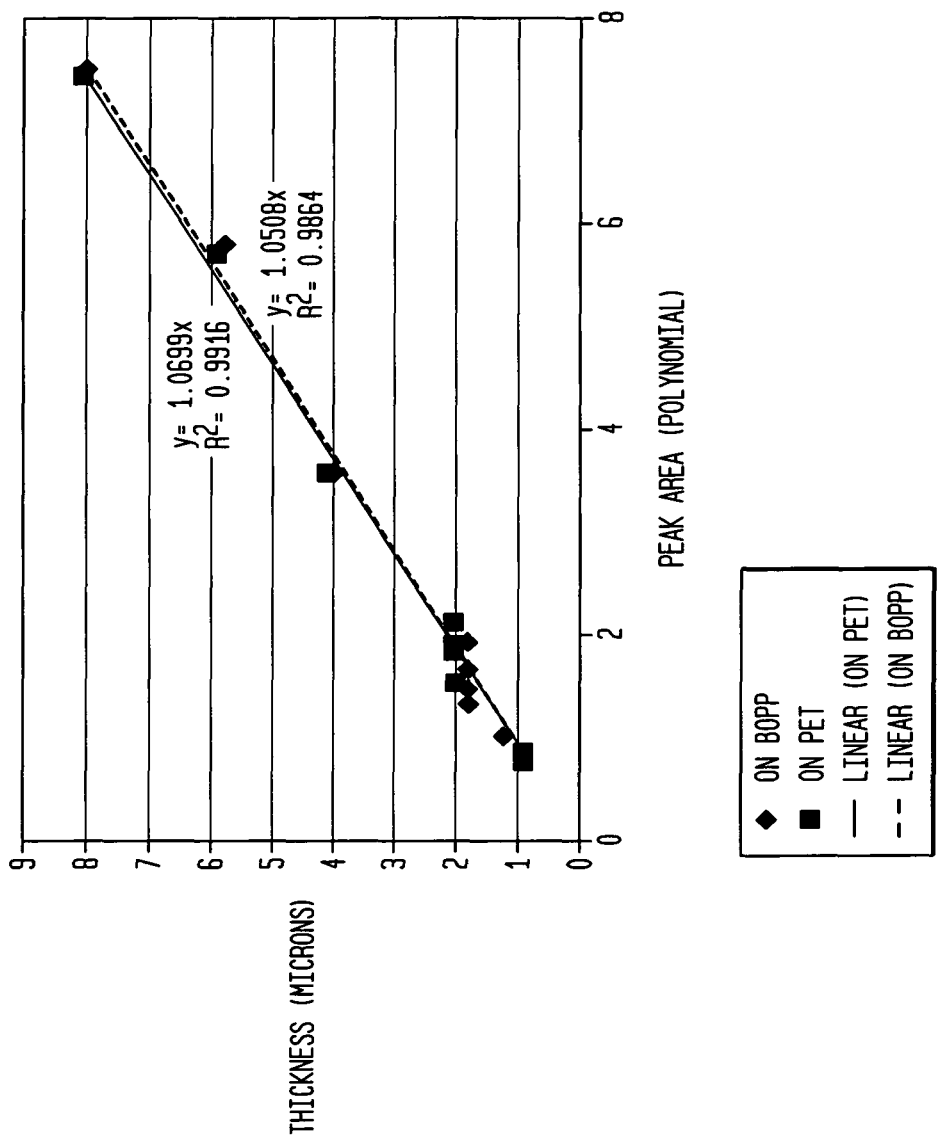
FIG. 20 shows a comparison of thickness vs. absorbance peak area of coatings on BOPP and PET films, which used coating compositions as described in Example 5 (concentrated polyester-montmorillonite coating composition with 8 percent total solids containing 20 mg/L SDB 4927 dye, which resulted in 35 weight percent montmorillonite in the dried film)

Barrier Coating Example 7: SDB 4927 Dye Containing Coating Compositions of Example 3C to Correlate Absorbance Spectra and Thickness on BOPP and PET Films The SDB 4927 dye at 20 mg/L concentration in the coating composition otherwise similar to Example 3C was cast on BOPP and PET films and absorbance spectra were measured. The coating thickness measurement was made using optical profilometry. The thickness was correlated with absorbance spectrum measured from the coating. As shown in FIG. 20, peak area of the dye with thickness on the film follows almost the same linearity (1.07 in PET and 1.05 in BOPP substrate) as on glass (1.09).

Figure 21:
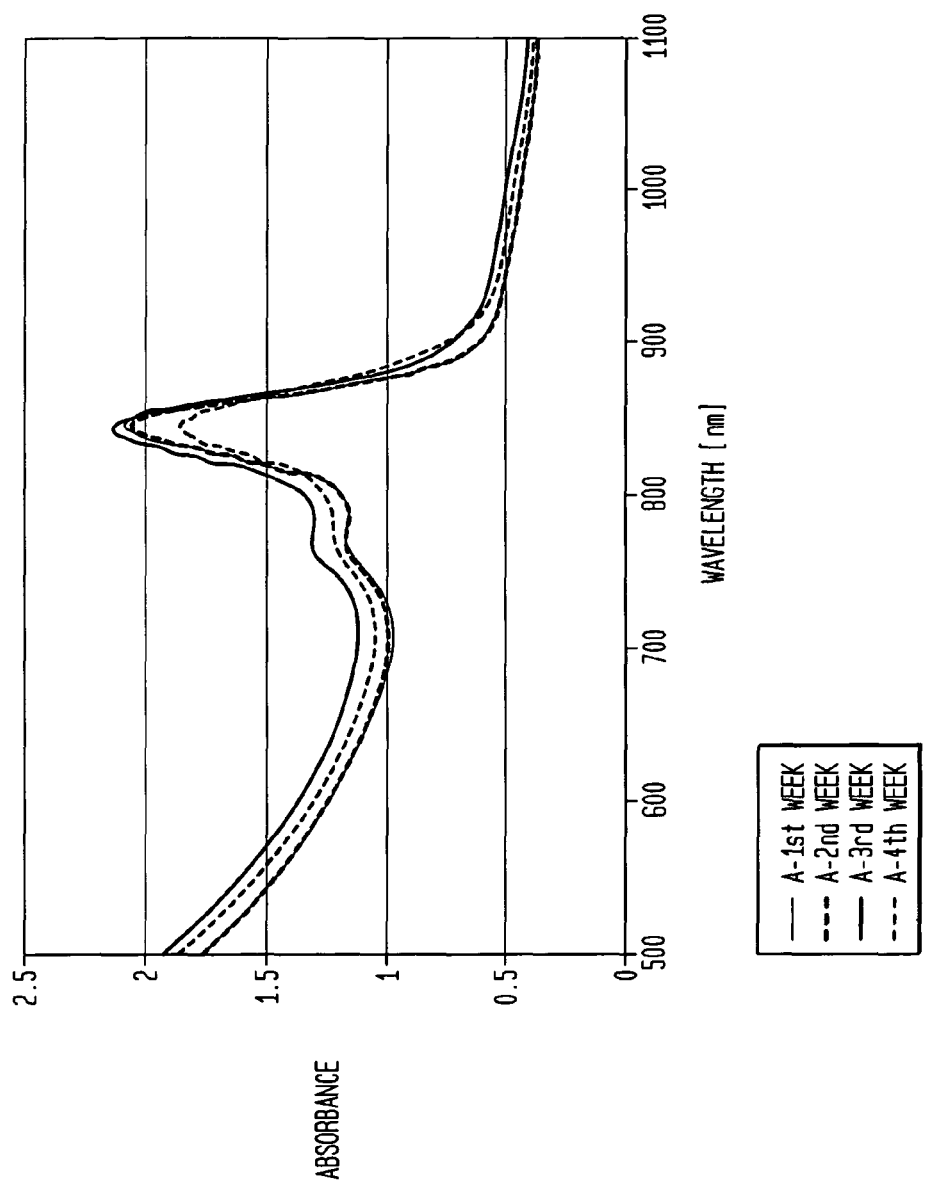
FIG. 21 shows absorption spectra of a diluted dye containing coating composition over time (see Barrier Coating Example 8 below for more details)

Barrier Coating Example 8: Stability Studies of SDB 4927 Dye Containing Coating Compositions of Example 3C A formulation containing SDB 4927 dye at 20 mg/L concentration in the coating composition otherwise similar to Example 3C was prepared. Spectra of this formulation diluted with water were measured periodically. The dye appears stable and the absorbance spectrum of dye in formulation has not changed for four weeks. For the same concentration of the dye in formulation, peak area remains the same as evident from FIG. 21. The observed absorbance peak area over time is also summarized in Table 8.

TABLE 8

| | Absorbance Peak Area |
|---|---|
| Time (week) | Absorbance peak area |
| 0 | 99.2 |
| 1 | 97.7 |
| 2 | 103.0 |
| 3 | 101.0 |
| 4 | 96.9 |
| 6 | 94.6 |
| 8 | 93.2 |
| Std deviation | 3.45 |

Example 9

Thickness Measurement for Thin Films, <1 Micron

The SBD 4927 dye at different concentrations in coating compositions otherwise similar to Example 3C were cast on BOPP substrate film and absorbance spectra were measured and compared. Specifically, the NIR dye SDB 4927 was added to the nanocomposite dispersion to measure the thickness of coating of very thin films (<1μ) using 50 mg/l dye and 20 mg/l dye. For the 50 mg/l dye compositions, the dye was added to the dispersion in a glass bottle and stirred using magnetic stirrer for approximately 7 hrs. at room temperature.

FIG. 22 shows the comparison of absorbance spectra of films (<1μ). It is clear from FIG. 22 that the peak of NIR dye is much more well defined when the dye concentration was increased from 20 to 50 mg/l.

Absorbance spectra were measured at different points on the film along with thicknesses using optical profilometry. Absorbance spectra and film thickness were measured at the same point within error. The peak area was correlated with thickness measured by profilometry as shown in FIG. 23. It is seen in FIG. 23 that the peak area of the dye is linear with thickness of coating, much the same as our previous results of coating on glass slide with 20 mg/l dye in thicker films. If we correlate the slope of absorbance peak area vs. thickness (profilometry) for two different concentrations of dye (20 and 50 mg/l), and scale to 20 mg/l, they are determined to be about 1 (see FIG. 12, FIG. 13) and 0.95 (=0.38×50/20, FIG. 23), respectively, showing good agreement. So also, the profilometry thickness values correspond to thickness determined by the spectrophotometer method of this invention as is seen in FIG. 24.

It is seen in this Example series that elevated levels of invisible marker dye may be used for thickness measurements of less than 1 micron. In general, the technique may be used to measure thicknesses of thin coatings by increasing the dye concentration in the liquid composite prior to coating to greater than 20 mg/l when thin films are employed. Dye concentrations of greater than 25 mg/l up to 75 mg/l are believed particularly suitable for barrier coating thicknesses of from 0.1-1 microns.

While the invention has been described in connection with numerous embodiments and aspects, modifications within the spirit and scope of the present invention, set forth in the appended claims, will be readily apparent to those of skill in the art.

What is claimed is:

1. An evacuated container assembly suitable for use in connection with biological sample collection comprising:
   (a) a container member formed of a first polymeric material and having a sidewall defining a cavity with an inner surface as well as one or more open ends;
   (b) a nanocomposite barrier coating disposed on a container member surface having a thickness of up to about 30 microns and being derived from an aqueous dispersion including (i) a dispersed barrier matrix polymer; and (ii) a substantially exfoliated silicate filler having an aspect ratio of more than 50; and
   (c) a sealing member disposed in the opening(s) of the container member operative to hermetically seal the cavity;
   wherein the cavity is evacuated and maintains a pressure below atmospheric pressure and exhibits a draw volume loss lower than that of a like assembly without a nanocomposite barrier film by a factor of at least 1.5.

2. The evacuated container assembly according to claim 1, wherein the assembly is used in connection with blood collection.

3. The evacuated container assembly according to claim 1, wherein the assembly exhibits a draw volume loss lower than that of like assembly without a nanocomposite barrier film by a factor of at least 2.

4. The evacuated container assembly according to claim 1, wherein the assembly exhibits a draw volume loss lower than that of like assembly without a nanocomposite barrier film by a factor of at least 5.

5. The evacuated container assembly according to claim 1, wherein the assembly exhibits a draw volume loss lower than that of like assembly without a nanocomposite barrier film by a factor of at least 10.

6. The evacuated container assembly according to claim 1, wherein the assembly exhibits a draw volume loss lower than that of like assembly without a nanocomposite barrier film by a factor of at least 25.

7. The evacuated container assembly according to claim 1, wherein the assembly exhibits a draw volume loss lower than that of like assembly without a nanocomposite barrier film by a factor of at least 40 up to a factor of 100.

8. The evacuated container assembly according to claim 1, having an overall length, a predetermined volume, as well as an outside diameter and wherein the sealing member is needle pierceable.

9. The evacuated container assembly of claim 8, wherein the outside diameter is between 5 and 15 mm.

10. The evacuated container assembly of claim 8, wherein the total length is between 40 mm and 140 mm.

11. The evacuated container assembly of claim 8, wherein the maximum fill volume is between 400 ml and 30 cc.

12. The evacuated container assembly of claim 8, wherein the maximum fill volume is between 2 and 10 cc.

13. The evacuated container assembly of claim 1, wherein the sidewall has an average thickness between 5 mm and 1.5 mm, wherein a thickness of the nanocomposite barrier coating is less than 20 microns.

14. The evacuated container assembly of claim 1, wherein an average combined thickness of the barrier coating and the container member is less than 1.5 mm, and the percentage of the thickness contributed by the coating is less than 4% of the thickness.

15. The evacuated container assembly of claim 14, wherein the percentage of the thickness contributed by the coating is less than 3% of the thickness.

16. The evacuated container assembly of claim 14, wherein the percentage of the thickness contributed by the coating is less than 2% of the thickness.

17. The evacuated container assembly according to claim 1, wherein the container inner cavity has a clot-affecting material therein.

18. The evacuated container assembly according to claim 17, wherein the clot-affecting material is an anticoagulant.

19. The evacuated container assembly according to claim 18, wherein the anticoagulant is chosen from the group consisting of heparin, citrate, EDTA, CTAD and combinations thereof.

20. The evacuated container assembly according to claim 17, wherein the clot affecting material is a coagulant.

21. The evacuated container assembly according to claim 17, wherein the coagulant is chosen from the group of silica, thrombin, snake venom and combinations thereof.

22. The evacuated container assembly container according to claim 1, further comprising a topcoat layer disposed on the nanocomposite barrier coating.

23. The evacuated container assembly according to claim 22, wherein the topcoat layer comprises a vinyl acrylic resin.

24. The evacuated container assembly according to claim 1, further comprising an adhesive layer disposed between the container body and the nanocomposite barrier coating.

25. The evacuated container assembly according to claim 24, wherein the adhesive layer comprises a urethane resin.

26. The evacuated container assembly according to claim 24, wherein the adhesive layer comprises a surface modified by gas plasma treatment.

27. The evacuated container assembly according to claim 1, wherein the container member comprises a polyolefin based polymer.

28. The evacuated container assembly according to claim 1, wherein the container member comprises a polyester based polymer.

29. The evacuated container assembly according to claim 1, wherein the container member comprises a polymer selected form polypropylenes, polyethylene terephthalates and cyclic olefin copolymers.

30. The evacuated container assembly according to claim 1, wherein the container member is formed from polypropylene.

31. The evacuated container assembly according to claim 1, wherein the nanocomposite barrier coating has a thickness of up to 30 microns.

32. The evacuated container assembly according to claim 1, wherein the nanocomposite barrier coating has a thickness of from 2-20 microns.

33. The evacuated container assembly according to claim 1, wherein the nanocomposite barrier coating has a thickness of from 3-10 microns.

34. The evacuated container assembly container according to claim 1, wherein the nanocomposite barrier coating has a thickness of from 4-6 microns.

35. The evacuated container assembly according to claim 1, wherein the exfoliated silicate filler material includes a compound selected from the group consisting of bentonite, vermiculite, montmorillonite, nontronite, beidellite, volkonskoite, hectorite, saponite, laponite, sauconite, magadiite, kenyaite, ledikite, and combinations thereof.

36. The evacuated container assembly according to claim 1, wherein the exfoliated silicate filler material includes montmorillonite.

37. The evacuated container assembly according to claim 1, wherein the exfoliated silicate filler material comprises platelets with an average aspect ratio of at least 100.

38. The evacuated container assembly according to claim 1, wherein the exfoliated silicate filler material comprises platelets with an average aspect ratio of at least 250.

39. The evacuated container assembly according to claim 1, wherein the exfoliated silicate filler material comprises platelets with an average aspect ratio of at least 500.

40. The evacuated container assembly according to claim 1, wherein the exfoliated silicate filler material comprises platelets with an average aspect ratio of at least 1,000.

41. The evacuated container assembly container according to claim 1, wherein the exfoliated silicate filler material comprises platelets with an average aspect ratio of at least 5,000.

42. The evacuated container assembly according to claim 1, wherein the barrier matrix polymer includes a polymer selected from the group consisting of polyesters, polyamides, chlorinated polymers, polyolefins, polyurethanes, polyethers, polyketones, polycarbonates, acrylics, vinylics, fluoropolymers, and combinations thereof.

43. The evacuated container assembly tubular container according to claim 1, wherein the barrier matrix polymer includes a polyester resin.

44. The evacuated container assembly according to claim 1, wherein the barrier matrix polymer includes a sulfonated polyester resin.

45. The evacuated container assembly according to claim 1, wherein the barrier coating exhibits a characteristic oxygen permeability of less than 0.02 cc-mm/m²-day-atm.

46. The evacuated container assembly according to claim 1, wherein the coating exhibits a characteristic oxygen permeability of less than 0.01 cc-mm/m²-day-atm.

47. The evacuated container assembly according to claim 1, wherein
the nanocomposite gas barrier coating disposed on the container member derived from an aqueous dispersion includes an invisible marker water soluble dye,
wherein the invisible marker dye is selected and present in amounts effective to indicate the thickness of the coating and thereby uniformity thereof.

48. The evacuated container assembly according to claim 47, wherein the invisible marker dye has an absorption peak in the near infrared (NIR) region of the electromagnetic spectrum.

49. The evacuated container assembly according to claim 47, wherein the invisible marker dye has an absorption peak in the region of greater than about 700 nm to about 1200 nm.

50. The evacuated container assembly according to claim 47, wherein the invisible marker dye has an absorption peak in the region of about 750 nm to about 1000 nm.

51. The evacuated container assembly according to claim 47, wherein the invisible marker dye has an absorption peak in the region of about 750 nm to about 850 nm.

52. The evacuated container assembly according to claim 1,
wherein said nanocomposite barrier coating is prepared from an aqueous dispersion which is concentrated by at least 5 percent by evaporating water from the dispersion prior to application on the container body.

53. The evacuated container assembly according to claim 1, prepared by way of a process comprising:
(a) providing a container member formed of a first polymeric material and having a closed bottom, an open top and a sidewall therebetween;
(b) treating the polymeric container member to increase its surface energy;
(b) applying an aqueous nanocomposite barrier coating composition directly to the treated surface, the aqueous nanocomposite barrier composition including (i) a dispersed barrier matrix polymer; and (ii) a substantially exfoliated silicate filler having an aspect ratio of more than 50.

54. The evacuated container assembly according to claim 53, wherein the polymeric container member is gas plasma treated prior to applying the nanocomposite barrier composition.

55. The evacuated container assembly according to claim 54, wherein the polymeric container member is flame plasma treated prior to applying the nanocomposite barrier composition.

56. The evacuated container assembly of claim 1, wherein the sidewall has an average thickness between 5 mm and 1.5 mm, wherein a thickness of the nanocomposite barrier coating is less than 10 microns.

57. The evacuated container assembly of claim 1, wherein the sidewall has an average thickness between 5 mm and 1.5 mm, wherein a thickness of the nanocomposite barrier coating is less than 6 microns.

58. The evacuated container assembly as claimed in claim 1, wherein the substantially exfoliated filler material is present at between 20% to 50% by weight of the total solids of the nanocomposite barrier coating.

* * * * *